(12) United States Patent
Armington et al.

(10) Patent No.: US 11,925,545 B2
(45) Date of Patent: Mar. 12, 2024

(54) ADJUSTABLE FIXATION DEVICE

(71) Applicant: Parcus Medical, LLC, Sarasota, FL (US)

(72) Inventors: Samuel Armington, Gainesville, FL (US); Mark D. Brunsvold, Sarasota, FL (US)

(73) Assignee: Parcus Medical, LLC, Sarasota, FL (US)

( * ) Notice: Subject to any disclaimer, the term of this patent is extended or adjusted under 35 U.S.C. 154(b) by 837 days.

(21) Appl. No.: 16/940,064

(22) Filed: Jul. 27, 2020

(65) Prior Publication Data

US 2021/0113324 A1    Apr. 22, 2021

Related U.S. Application Data

(63) Continuation of application No. 16/207,652, filed on Dec. 3, 2018, now Pat. No. 10,722,344, which is a continuation-in-part of application No. PCT/US2017/035855, filed on Jun. 2, 2017.

(60) Provisional application No. 62/612,518, filed on Dec. 31, 2017, provisional application No. 62/405,912, filed on Oct. 8, 2016, provisional application No. 62/344,510, filed on Jun. 2, 2016.

(51) Int. Cl.
| | | |
|---|---|---|
| *A61F 2/08* | (2006.01) | |
| *A61B 17/04* | (2006.01) | |
| *A61B 17/06* | (2006.01) | |
| *A61B 17/58* | (2006.01) | |
| *A61B 17/68* | (2006.01) | |
| *A61F 2/42* | (2006.01) | |

(52) U.S. Cl.
CPC ........ *A61F 2/0811* (2013.01); *A61B 17/0401* (2013.01); *A61B 17/0482* (2013.01); *A61B 17/06166* (2013.01); *A61B 17/58* (2013.01); *A61B 17/683* (2013.01); *A61F 2/4202* (2013.01); *A61B 2017/0404* (2013.01); *A61B 2017/0414* (2013.01); *A61B 2017/0459* (2013.01); *A61B 2017/0477* (2013.01); *A61B 17/0485* (2013.01); *A61B 2017/0496* (2013.01); *A61B 2017/0618* (2013.01); *A61B 2017/06185* (2013.01); *A61F 2002/0852* (2013.01); *A61F 2002/0882* (2013.01); *A61F 2220/0075* (2013.01); *A61F 2250/0007* (2013.01); *A61F 2250/0012* (2013.01)

(58) Field of Classification Search
CPC . A61B 17/0401; A61B 17/58; A61B 2017/04; A61B 2017/0496; A61F 2/0811; A61F 2/4202; A61F 2002/0852
See application file for complete search history.

(56) References Cited

U.S. PATENT DOCUMENTS

| | | | |
|---|---|---|---|
| 4,976,013 A | * | 12/1990 | Wax ..................... F16G 11/046 24/129 R |
| 7,150,757 B2 | | 12/2006 | Fallin et al. |
| 7,585,311 B2 | | 9/2009 | Green et al. |

(Continued)

*Primary Examiner* — Julian W Woo
*Assistant Examiner* — Osama Nemer
(74) *Attorney, Agent, or Firm* — Goodwin Procter LLP

(57) ABSTRACT

An adjustable fixation device includes a cleat portion and a suture portion, where the suture portion has a loop portion and a suture tail. Pulling on the suture tail places in tension a graft coupled to the loop portion. The suture is arranged to convey a mechanical advantage so that substantial force can be readily and controllably applied to the graft.

17 Claims, 48 Drawing Sheets

(56) References Cited

U.S. PATENT DOCUMENTS

| | | | |
|---|---|---|---|
| 7,594,923 B2* | 9/2009 | Fallin | A61B 17/0401 |
| | | | 606/103 |
| 7,601,165 B2 | 10/2009 | Stone | |
| 7,867,261 B2 | 1/2011 | Sixto, Jr. et al. | |
| 8,162,997 B2 | 4/2012 | Struhl | |
| 8,323,338 B2 | 12/2012 | LeBeau et al. | |
| 9,265,498 B2* | 2/2016 | Fallin | A61B 17/0487 |
| 9,717,587 B2 | 8/2017 | Dougherty et al. | |
| 9,782,250 B2 | 10/2017 | Dougherty et al. | |
| 9,999,496 B2 | 6/2018 | Dougherty et al. | |
| 10,149,752 B2 | 12/2018 | Dougherty et al. | |
| 2008/0065114 A1 | 3/2008 | Stone et al. | |
| 2010/0125297 A1* | 5/2010 | Guederian | A61B 17/0401 |
| | | | 606/232 |
| 2010/0256677 A1 | 10/2010 | Albertorio et al. | |
| 2012/0065731 A1* | 3/2012 | Justin | A61F 2/0811 |
| | | | 623/13.14 |
| 2012/0109194 A1 | 5/2012 | Miller et al. | |
| 2012/0123474 A1* | 5/2012 | Zajac | A61B 17/842 |
| | | | 606/232 |
| 2013/0035720 A1 | 2/2013 | Perriello et al. | |
| 2014/0128921 A1 | 5/2014 | Parsons et al. | |
| 2017/0319327 A1 | 11/2017 | Dougherty et al. | |
| 2019/0053888 A1 | 2/2019 | Dougherty et al. | |
| 2021/0068806 A1* | 3/2021 | Niver | A61B 17/8057 |

* cited by examiner

ADJUSTABLE FIXATION DEVICE

CROSS-REFERENCE TO RELATED APPLICATIONS

This application is a continuation of U.S. application Ser. No. 16/207,652 filed Dec. 3, 2018, which is a bypass continuation-in-part of International application no. PCT/US2017/035855 filed on Jun. 2, 2017, which claims the benefit of U.S. provisional patent application No. 62/344,510 filed on Jun. 2, 2016, and claims the benefit of U.S. provisional patent application No. 62/405,912 filed on Oct. 8, 2016, and this application also claims the benefit of U.S. provisional patent application No. 62/612,518 filed on Dec. 31, 2017, the disclosures of which are hereby incorporated by reference in their entireties.

FIELD OF THE INVENTION

The present invention relates to adjustable fixation devices and more particularly to an adjustable graft fixation devices for surgical applications.

BACKGROUND OF THE INVENTION

The ability to fix tissue effectively is central to the surgical process. In surgery, and in particular in arthroscopic surgery, fixation of tissue must be achieved under constraints of limited access. It is understood by those of skill in the art that fixation failure is a particularly important failure mode in the early postoperative period, and although many fixation approaches have been developed, the need for continued improvement remains widely acknowledged.

While a variety of techniques have been developed for coupling grafts of soft tissue to bone, it remains difficult to achieve good results in certain particularly demanding procedures. For example, the repair of an anterior cruciate ligament is a surgical procedure where the parameters of graft tension and graft positioning have a strong bearing on surgical results.

SUMMARY OF THE INVENTION

An adjustable fixation device includes a cleat comprising first and second cleat openings and a connector seat between the openings. A flexible connector can have first and second cleat loops through the first and second openings of the cleat and a tensioning end portion. The connector comprises an intra-connector sliding loop engagement portion and a connector-device sliding loop engagement portion. The tensioning end portion of the flexible connector further comprises an axial sliding connector-connector engagement portion and a transverse sliding connector-connector engagement portion transversely engaging the first and second cleat loops and extending between portions of the cleat loops and the connector seat. The flexible connector can be a suture.

The axial sliding connector-connector engagement portion can include a portion of the tensioning end being positioned in an axial channel through a portion of a cleat loop. The axial channel can be formed by axial threading of the tensioning end through the portion of the cleat loop.

The transverse sliding connector-connector engagement portion can include a portion of the tensioning end being transversely threaded through a cleat loop. The transverse sliding connector-connector engagement portion can include a portion of the tensioning end being positioned in a transverse channel through a portion of a cleat loop. The transverse channel can be formed by transverse threading of the tensioning end through the connector-connector engagement portion of the cleat loop.

At least one of said first and second cleat openings can be tapered. The cleat can further include lateral guide holes for receiving guiding sutures.

A protective cover can be provided for the flexible connector at a portion of the flexible connector comprising at least one selected from the group consisting of the intra-connector sliding loop engagement portion and the connector-device sliding loop engagement portion. The protective cover reduces friction and chafing.

An adjustable fixation system includes an adjustable fixation device. The adjustable fixation device can include a cleat comprising first and second cleat openings and a connector seat between the openings. A flexible connector having first and second cleat loops through the first and second openings of the cleat and has a tensioning end portion. The connector can include an intra-connector sliding loop engagement portion and a connector-device sliding loop engagement portion. The tensioning end portion of the flexible connector further can include an axial sliding connector-connector engagement portion and a transverse sliding connector-connector engagement portion transversely engaging the first and second cleat loops and extending between portions of the cleat loops and the connector seat. An implantable medical device is slidably connected to the adjustable fixation device at the connector-device sliding loop engagement portion.

The implantable device can be a graft. The implantable medical device can be a second cleat comprising first and second holes. The connector-device engagement portion of the flexible connector can be threaded through one of the holes in a first direction and through the other of the holes in a second direction forming a sliding connector-device engagement. The implantable medical device can include a plate comprising first and second holes. The connector-device engagement portion of the flexible connector can be threaded through one of the holes in a first direction and through the other of the holes in a second direction forming a sliding connector-device engagement.

The adjustable fixation system can further include a second adjustable fixation device having a second connector-device sliding loop engagement portion. The implantable medical device can be slidably connected between the connector-device sliding loop engagement portion of the adjustable fixation device and the connector-device sliding loop engagement portion of the second adjustable fixation device.

A method for the adjustable fixation of an implantable medical device can include the step of providing an adjustable fixation device which includes a cleat comprising first and second cleat openings and a connector seat between the openings, and a flexible connector. The flexible connector can have first and second cleat loops through the first and second openings of the cleat and a tensioning end portion. The connector can include an intra-connector sliding loop engagement portion and a connector-device sliding loop engagement portion. The tensioning end portion of the flexible connector can further include axial sliding connector-connector engagement portion and a transverse sliding connector-connector engagement portion transversely engaging the first and second cleat loops and extending between portions of the cleat loops and the connector seat.

The method also includes slidably connecting an implantable medical device to the adjustable fixation device at the connector-device sliding loop engagement portion. The adjustable fixation device and the implantable medical device are positioned in the body of the patient. A tensioning force is applied to the tensioning end portion of the flexible connector to tighten and secure the adjustable fixation device and the implantable medical device in position in the body of the patient.

The flexible connector can be a suture. The axial sliding connector-connector engagement portion can include a portion of the tensioning end being positioned in an axial channel through a portion of a cleat loop. The axial channel can be formed by axial threading of the tensioning end through the portion of the cleat loop. The transverse sliding connector-connector engagement portion can include a portion of the tensioning end being transversely threaded through a cleat loop. The transverse sliding connector-connector engagement portion can include a portion of the tensioning end being positioned in a transverse channel through a portion of a cleat loop. The transverse channel can be formed by transverse threading of the tensioning end through the connector-connector engagement portion of the cleat loop.

The method can be used for a number of different surgical repair procedures. These include, but are not limited to, anterior cruciate ligament (ACL) repair, syndesmosis repair and ligamentum teres repair.

An adjustable fixation device can include a cleat, said cleat including a body member, the body member having an upper surface and a lower surface, the upper surface being disposed in substantially parallel spaced relation to the lower surface, the cleat having disposed therethrough between the upper and lower surfaces a first symmetric hole and a second tapered hole; and a suture portion, wherein a first region of the suture portion is disposed within the first symmetric hole and a second region of the suture portion is disposed within the tapered hole, the suture being configured to include an adjustable splice. The suture portion can further include a loop portion. The loop portion can be disposed coaxially within a sheath. The sheath can include first and second tails for fixing a graft adjacent to the loop portion of said suture portion.

An adjustable fixation device can include a cleat portion and a suture portion, the suture portion including a suture tail, the suture tail being configured, when placed in tension, to tighten a loop of the suture portion so as to convey a mechanical advantage from the tail portion to the loop. The adjustable fixation device can provide a 4:1 mechanical advantage. The loop portion can be disposed on a first side of the cleat portion and the tail portion can be disposed on a second opposite side of the cleat portion, whereby the tail may be placed in tension after the cleat portion is installed to support a surgical graft with the loop portion.

BRIEF DESCRIPTION OF THE DRAWINGS

There are shown in the drawings embodiments that are presently preferred it being understood that the invention is not limited to the arrangements and instrumentalities shown, wherein.

DETAILED DESCRIPTION OF THE INVENTION

Figure 1:
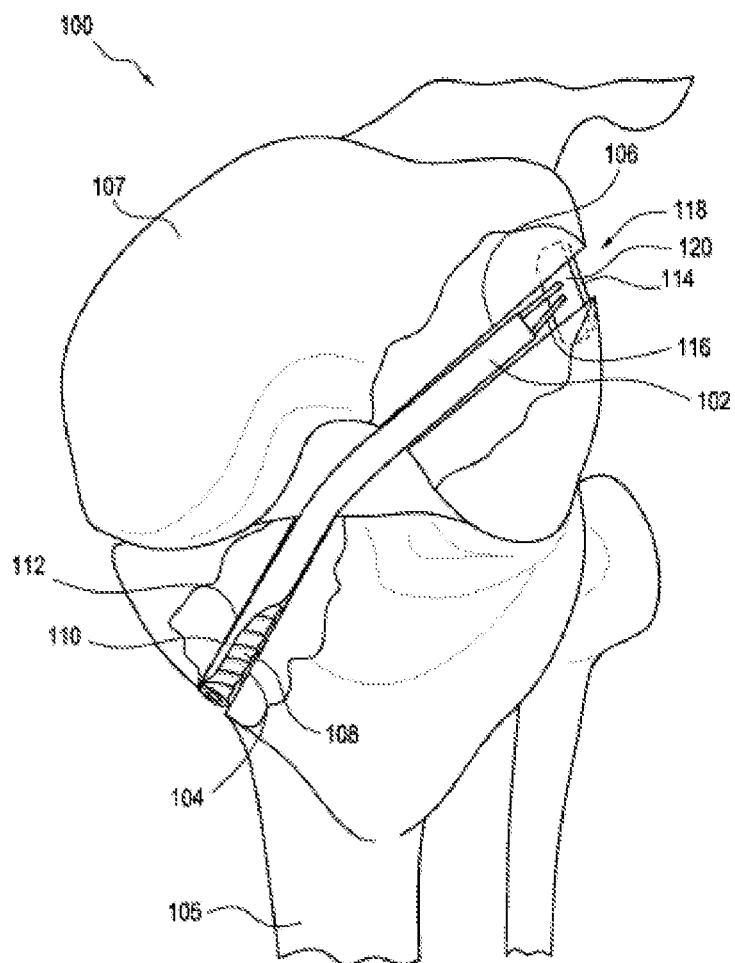
FIG. 1 shows, in schematic view, an exemplary adjustable fixation device prepared according to principles of the invention.

In the following description, for purposes of explanation, numerous specific details are set forth in order to provide a thorough understanding of the present invention. It will be apparent, however, to one skilled in the art that the present invention may be practiced without these specific details. It should be noted that, while the various figures show respective aspects of the invention, no one figure is intended to show the entire invention. Rather, the figures together illustrate the invention in its various aspects and principles. As such, it should not be presumed that any particular figure is exclusively related to a discrete aspect or species of the invention. To the contrary, one of skill in the art would appreciate that the figures taken together reflect various embodiments exemplifying the invention.

Referenced throughout the specification to "one embodiment" or "an embodiment" means that a particular feature, structure, or characteristic described in connection with the embodiment is included in at least one embodiment of the present invention. Thus, the appearance of the phrases "in one embodiment" or "in an embodiment" in various places throughout the specification are not necessarily all referring to the same embodiment. Furthermore, the particular features, structures, or characteristics may be combined in any suitable manner in one or more embodiments. Directional references such as upward and downward are provided for purposes of a reference for description, and it should be understood that the invention can be oriented in any direction within the body.

For clarity of disclosure, the terms "flat oval" and "tapered flat oval" are now defined. The term "flat oval" is intended to describe a geometric shape including two semicircles of equal radius joined at their open ends by first and second line segments of equal length. The term tapered flat oval is intended to describe a geometric shape including two approximate semicircles of unequal radius joined at their open ends by first and second line segments of equal length.

An adjustable fixation device according to the invention can include a cleat comprising first and second cleat openings and a connector seat between the openings. A flexible connector can form first and second cleat loops through the first and second openings of the cleat and a tensioning end portion. The connector can include an intra-connector sliding loop engagement portion and a connector-device sliding loop engagement portion. The tensioning end portion of the flexible connector can further comprise an axial sliding connector-connector engagement portion and a transverse sliding connector-connector engagement portion transversely engaging the first and second cleat loops and extending between portions of the cleat loops and the connector seat.

The flexible connector can be of many suitable constructions and materials. The flexible connector can be braided or single filament. The dimensions of the flexible connector can vary depending on the repair that is being performed and the strength and dimensions necessary for the repair. The flexible connector can be made from any suitable flexible medical grade material, including polymeric materials and flexible metal materials. The flexible connector can be a suture, and in this application the terms suture and flexible connector will sometimes be used interchangeably.

The axial sliding connector-connector engagement portion can have a portion of the tensioning end positioned in an axial channel through a portion of a cleat loop. The axial channel can be formed by axial threading of the tensioning end through the portion of the cleat loop. The transverse sliding connector-connector engagement portion can include a portion of the tensioning end being transversely threaded through a cleat loop. The transverse sliding connector-connector engagement portion can include a portion of the tensioning end being positioned in a transverse channel through a portion of a cleat loop. The transverse channel can be formed by transverse threading of the tensioning end through the connector-connector engagement portion of the cleat loop. The cleat can further include lateral guide holes for receiving guiding sutures for use in positioning the adjustable fixation device at the target location.

An implantable medical device is slidably connected to the adjustable fixation device at the connector-device sliding loop engagement portion. The implantable medical device can be selected from many different implantable medical devices. One such implantable device is a graft. The implantable medical device can be a second cleat. The second cleat can have for example first and second holes. The connector-device engagement portion of the flexible connector can be threaded through one of the holes in a first direction and through the other of the holes in a second direction forming a sliding connector-device engagement.

The implantable medical device can include a second cleat, plate or other structure comprising first and second holes, and wherein the connector-device engagement portion of the flexible connector is threaded through one of the holes in a first direction and through the other of the holes in a second direction forming a sliding connector-device engagement. Such a device can be used for example in syndesmosis repair procedures.

The adjustable fixation system can include a second adjustable fixation device having a second connector-device sliding loop engagement portion. The implantable medical device can be slidably connected between the connector-device sliding loop engagement portion of the adjustable fixation device and the connector-device sliding loop engagement portion of the second adjustable fixation device.

Modifications are possible. A covering portion can be provided over the flexible connector or the graft at the sliding engagement portions to minimize sliding friction or chafing from sliding friction. The cover can be a piece of protective suture through which the flexible connector portions are threaded, an external cover applied over these portions of the flexible connector, or a low friction protective coating composition applied to the flexible connector.

The axial and transverse sliding engagement of the sliding engagement portions of the flexible connector are shown as being formed by threading one portion of the flexible connector through another, axially or transversely. Such a sliding connection can also be accomplished by one or more fittings with channel portions through which the sliding connection can be accomplished. Such channel portions can be oriented axially or transversely as necessary. Such fittings can be provided in-line or crimped or otherwise attached to the flexible connector at the proper position.

A method for the adjustable fixation of an implantable medical device can include positioning the adjustable fixation device using guide sutures or some other placement apparatus such as forceps. The cleat is positioned against bone or some other body part that will provide resistance as tension is applied to the tensioning end portion. The opposing end of the implantable medical device is similarly secured. The implantable medical device can be slidably connected to the adjustable fixation device either before or after positioning of the adjustable fixation device at the target location. A tensioning force is then applied to the tensioning end portion of the flexible connector to tighten and secure the adjustable fixation device and the implantable medical device in position in the body of the patient.

The method of the invention can be used to perform a number of surgical procedures. These include anterior cruciate ligament (ACL) repair, and syndesmosis repair where the implantable medical device is a plate for engaging and supporting the fibula. The invention is useful for ligamentum teres reconstruction procedures, and for other procedures.

For example, in anterior cruciate ligament (ACL) repair, as illustrated schematically 100 in FIG. 1, a damaged ACL is removed and replaced by graft tissue 102. The graft tissue is disposed within first 104 and second 106 channels prepared in the tibia 105 and femur 107 respectively. The graft tissue 102 is, in the illustrated repair, coupled to the tibia 105 with an interference fixation where a helically threaded bone anchor 108 mechanically compresses a portion 110 of the graft tissue 102 between an external circumferential surface of the bone anchor 108 and an internal surface region 112 of the channel 104.

As shown, the graft tissue 102 is coupled to the femur 107 with a combination of a cleat 114 and a suture 116. The cleat 114 is disposed across an aperture 118 where the second channel 106 exits the femur. The cleat, sometimes referred to as a button, is substantially rigid and supports the suture 116 in tension. A proximal surface region 120 of the cleat is disposed in contact with corresponding surface regions of the bone surrounding aperture 118.

In various surgical repairs, and particularly in ACL repair, the forces borne by the graft are relatively large. Moreover, while it is desirable to stabilize the joint to allow healing, it is also important to maintain activity in a joint to avoid loss of range of motion. Consequently, it is important that the position and tension applied to the graft 102 is correct. Disadvantages of existing methods and apparatus include the difficulty involved in achieving a reliable coupling between soft tissue and bone, and ensuring that the ultimate graft assembly has both the right length and the right tension.

Through personal experience, analysis, and careful observation, the present inventors have come to understand that the effectiveness of tissue coupling in a wide variety of surgical procedures can be improved by providing a fixturing device that permits ready adjustment of the position and tension of soft tissue elements secured by the device. In response, the inventors have conceived and reduced to practice and adjustable surgical cleat and suture combination. Accordingly, the present invention includes an adjustable surgical cleat, and a combination of adjustable surgical cleat and suture.

According to the present invention, a combination of the splice and cleat design work together to provide a high breaking strength. The cleat features narrow, elongated openings designed to stack the suture onto itself to maintain consistency, and can include a v-shaped notch in one of the grooves designed to fasten the adjustment tail. The v-shape is specifically designed to clamp the tail without the need for a hard edge. This allows for a larger radius inside the cleat, which greatly reduces shearing between the suture and cleat. Also improving the product's breaking strength is the splice design itself. The design creates a 4:1 mechanical advantage at the adjustment tail and effectively distributes the load over more lengths of suture than comparable products.

Minimal elongation is achieved by combining the adjustable loop splice with the mechanical fixation of the tail. An inherent problem with alternative technologies and that of the loop splice itself is the slip of the tail back into the splice during cyclic loading. According to the present invention, to prevent 'tail slip', the tail is spliced beneath both lengths of suture at the cleat. This utilizes the tension on the loop to clamp the tail into the cleat's v shaped groove which nearly eliminates tail slip.

Another matter of elongation to be minimized is the initial displacement. As a product of the splice and suture weave tightening after an adjustment in length, the 4:1 mechanical advantage allows only a quarter of the splice's initial elongation to be translated into graft displacement. This is a tremendous advantage over earlier approaches, many of which translate initial splice elongation directly into graft displacement.

A great benefit of a 4:1 mechanical advantage splice design is its adjustability. It allows surgeons to apply tension to the graft far more easily than with competing products. Not only can tension be applied more easily, but greater tension can be applied, allowing surgeons improved adjustability when fixing a graft to bone. Furthermore, the single tail simplifies adjustment, and allows the surgeon a free hand while applying tension to the graft.

Figure 2:
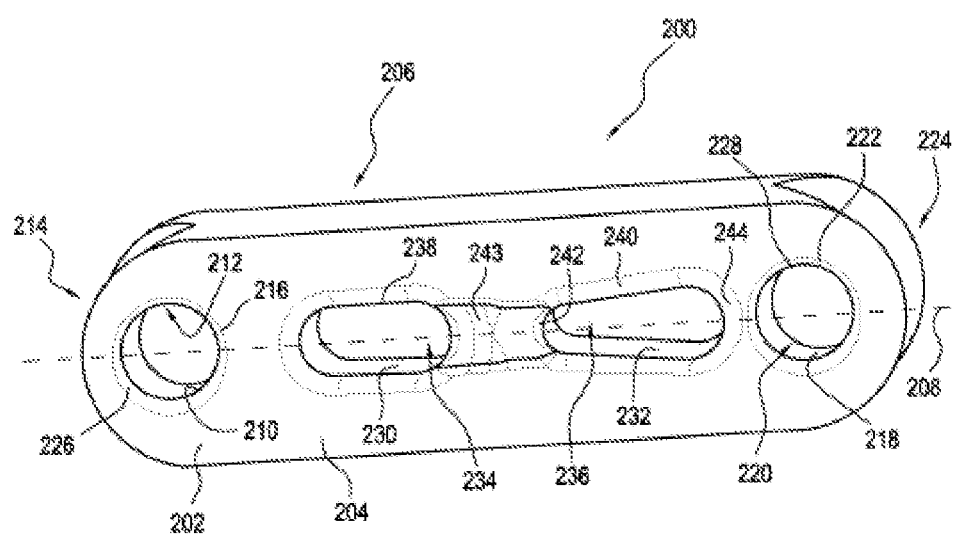
FIG. 2 shows, in schematic perspective view, an exemplary cleat portion of an exemplary adjustable fixation device prepared according to principles of the invention.

FIG. 2 shows, in schematic perspective view, an exemplary cleat 200 prepared according to principles of the invention. The cleat includes a body member 202 with an outer surface 204. An inner surface 206 is disposed in substantially parallel spaced relation to the outer surface 204.

In the illustrated embodiment, the body member 202 substantially exhibits mirror symmetry across a centerline 208 of the outer surface 204. It should be understood, however, that a wide variety of other shapes will be employed in alternative embodiments of the invention.

An internal circumferential surface 210 defines a bore 212 through the body member 202, between the outer surface 204 and the inner surface 206, generally proximate to a first end 214 of the body member. In the illustrated embodiment, the internal circumferential surface 210 defines respective generally circular apertures, e.g. 216, wherein meets the outer 204 and inner 206 surfaces. A corresponding internal surface 218 defines a similar bore 220 and similar apertures, e.g. 222 at a second opposite end 224 of the body member 202.

One of skill in the art will understand that alternative shapes of aperture 216, 222 are contemplated to be within the scope of the invention. Thus, the apertures may be polygonal, elliptical, stellate, randomly shape, etc. according to corresponding abundance of the invention. Moreover the apertures of first and second ends of the body member 202 may be differently shaped. Additionally, in certain embodiments one or more of the two apertures will be omitted, or additional apertures may be added that are not illustrated by the exemplary cleat 200.

As in the illustrated embodiment, in certain embodiments edges defining the apertures, e.g., 226, 228 will be chamfered or curved, or otherwise softened so as to reduce the likelihood of a suture being abraded or cut by the edge.

Two further internal surface regions 230, 232 define respective third 234 and fourth 236 bores through the body member 202, with corresponding apertures, e.g. 238, 240 at the outer 204 and inner surfaces 206. Like edges 226, 228, edges of apertures 238, 240, will be beveled, chamfered or curved in various embodiments of the invention.

Aperture 238 is substantially flat oval in shape. Aperture 240 is tapered flat oval in shape, and has a relatively smaller radius at its inner curve 242 as compared with its outer curve 244. Both the flat oval aperture 238 and the tapered flat oval aperture 240 have respective longitudinal axes. In the illustrated embodiment, these axes are substantially parallel to the centerline 208 of the outer surface 204 of the body member 202. It should be understood, however, that the longitudinal axes of the apertures 234, 236, and their orientation more generally with respect to the body member 202 will be different in different embodiments of the invention.

A recess or groove 243 is disposed between the proximate ends of aperture 234 and aperture 236. Groove 243 is generally concave, as viewed from the perspective of FIG. 2, and in certain embodiments, has edges that are chamfered or curved. As will be understood upon review of the further description below, apertures 234, 236, and groove 243 are sized to accommodate suture material for an adjustable cleat and suture combination.

In certain embodiments of the invention, body member 202 will include a titanium material. In other embodiments of the invention, body member 202 will include a PolyEther Ether Keystone (PEEK) material. In various embodiments of the invention, the material of body member 202 will include a bio-absorbable material and in other embodiments of the invention the body member 202 will include a non-bioabsorbable material. Any of a wide variety of biocompatible materials will be used in corresponding embodiments of the invention.

Figure 3A:
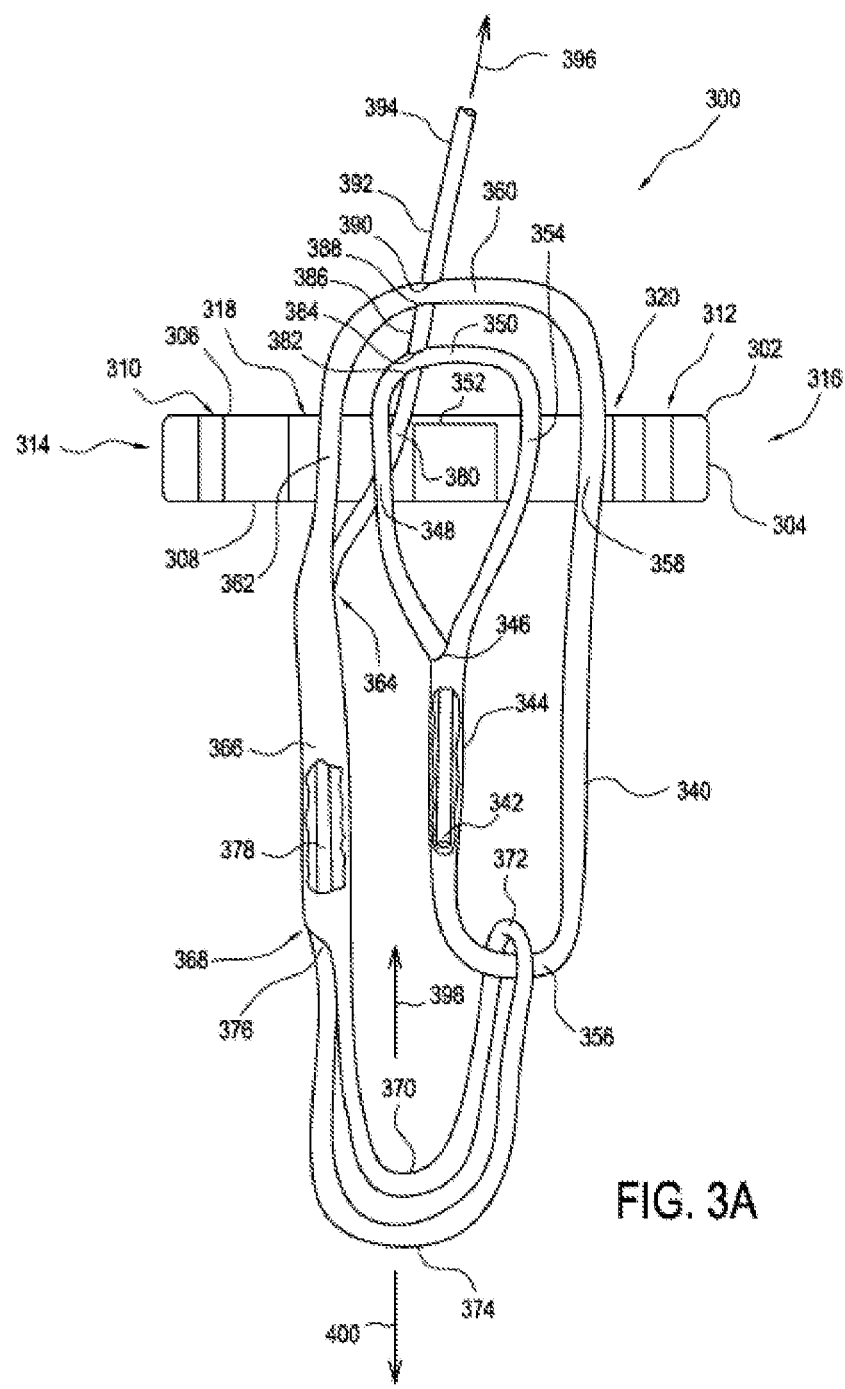
FIG. 3A shows, in schematic cross-section, portions of an adjustable fixation device including a cleat and a suture according to principles of the invention.

FIG. 3A shows, in schematic cross-section, portions of an adjustable fixation device 300 including a cleat 302 and a suture 340. The illustrated cleat, 302 is similar to cleat 200 of FIG. 2 and includes a body member 304, an outer surface region 306 and an inner surface region 308 disposed in substantially parallel spaced relation to one another. First 310 and second 312 outer bores connect the surface region 306, 308 each in relative to proximity to a respective end 314, 316 of the body member 304.

Also disposed between outer surface region 306 and inner surface region 308 are a third generally tapered flat oval bore 318 and a fourth generally flat oval bore 320.

As shown in cutaway view, a braided suture 340 has a first end 342 captured longitudinally within a portion 344 of the same suture. Proceeding from the captured end 342, the suture proceeds outwardly through an aperture 346 in a wall of the suture 340. Thereafter, a portion of the suture 348 is disposed within the tapered flat oval bore 318 of cleat 302 and passes 350 above a groove 352 of the cleat 302. Proceeding further along the suture 340 in the same direction, a portion 354 of the suture is disposed within flat oval aperture 320. Proceeding in the same direction, one passes again the aperture 346 and proceeds to a portion of the suture disposed in an upwardly facing U-shaped bend 356.

Proceeding thereafter in the same direction, a further portion 358 of the suture is disposed, once again, within flat-oval aperture 320 before a still further portion of the suture 360 is disposed once again above groove 352. Proceeding thereafter in the same direction, another portion of the suture 362 is disposed again within the tapered flat-oval aperture 318. Below this, is disposed a further aperture 364 in the wall of suture 340.

Proceeding in the same direction, and as will be described shortly, a portion 366 of the suture has a further portion disposed coaxially therewithin. Thereafter the suture proceeds, in the same direction, past a further aperture 368 to a further upwardly facing U-shaped bend portion of the suture 370.

Proceeding in the same direction, one arrives at a portion of the suture 372 disposed in a downwardly facing U-shaped bend intercoupled with upwardly facing U-shaped portion 356. Proceeding again in the same direction, an additional portion of the suture 374 forms a further upwardly facing U-shaped bend. Again, proceeding in the same direction, a portion 376 of the suture is disposed within aperture 368.

The next proceeding portion of the suture 378 is disposed coaxially within suture portion 366 and thereafter exits through aperture 364. Proceeding again in the same direction another portion 380 of suture 340 is disposed again within the tapered flat oval aperture 318 thereafter moving beyond the cleat 304 to pass into and immediately out of suture portion 350 transversely through respective apertures 382, 384, emerging as suture portion 386. Thereafter, suture 340 passes upwardly to pass into and immediately out of suture portion 360 transversely through aperture 388, 390 respectively, emerging as suture portion 392 which then forms a tail 394 of suture 340.

As will be further discussed below, pulling 396 on tail 394 tends to urge suture portion 370 and 374 upwardly 398 toward surface 308 with a substantial (four times) mechanical advantage. Accordingly, and again as will be further discussed below, coupling a graft to suture portions 370 and 374 allows positional adjustment and tensioning of the graft by pulling on tail 394 of suture 340.

Upon careful examination of FIG. 3A, it will be apparent to the practitioner of skill in the art that, upon tensioning of the suture by pulling 396 on tail 394, reactive forces 400 exerted by the graft will tend to pull suture portions 350 and 360 into groove 352 where they will tend to compress the suture portions passing through apertures 382, 384 and 388, 390, thereby preventing motion in the direction of the reactive forces 400. Likewise, constrictive forces applied to suture portion 378 by internal surface regions of suture portion 366 will tend to prevent such motion. Accordingly, a unidirectional apparatus is provided which allows tightening by pulling on tail 394 but which resists loosening in response to reactive forces 400.

Figure 3B:
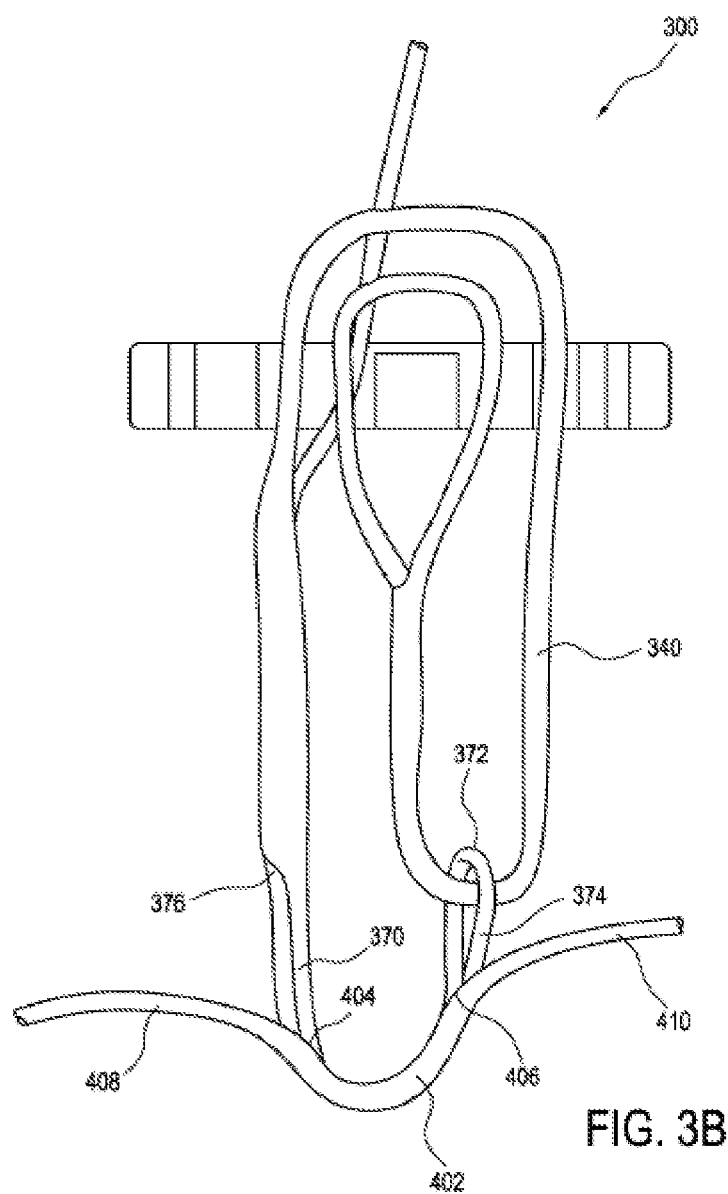
FIG. 3B shows a further aspect of an adjustable fixation device including a cleat and a suture according to principles of the invention.

FIG. 3B shows a further aspect of the invention in which suture portions 370 and 374 of fixation device 300, described above, are disposed within a covering suture portion 402. The covering suture portion serves to increase the surface area supporting a graft and reduce the opportunity for graft abrasion by suture portion 370 and 374.

As will be apparent upon examination of the figure, and proceeding in the direction previously established suture portion 370 of suture 340 passes inward through an aperture 404 of cover suture portion 402 and proceeds generally coaxial to portion 402 until exiting from cover portion 402 through aperture 406 thereafter, suture 340 proceeds through previously-identified inverted U-shared bend 372 and thereafter, as suture portion 374 reenters aperture 406. Suture 340 then proceeds substantially coaxially within suture portion 402 reemerging from aperture 404 as suture portion 376.

Apertures 404 and 406 are disposed medially within suture portion 402, such that the extremities of suture portion 402 form respective tails 408, 410. As will be further discussed in relation to FIG. 4C, tails 408 and 410 are beneficially applied in securing a graft to the assembly of suture portions 370, 374 and 402.

Figure 3C:
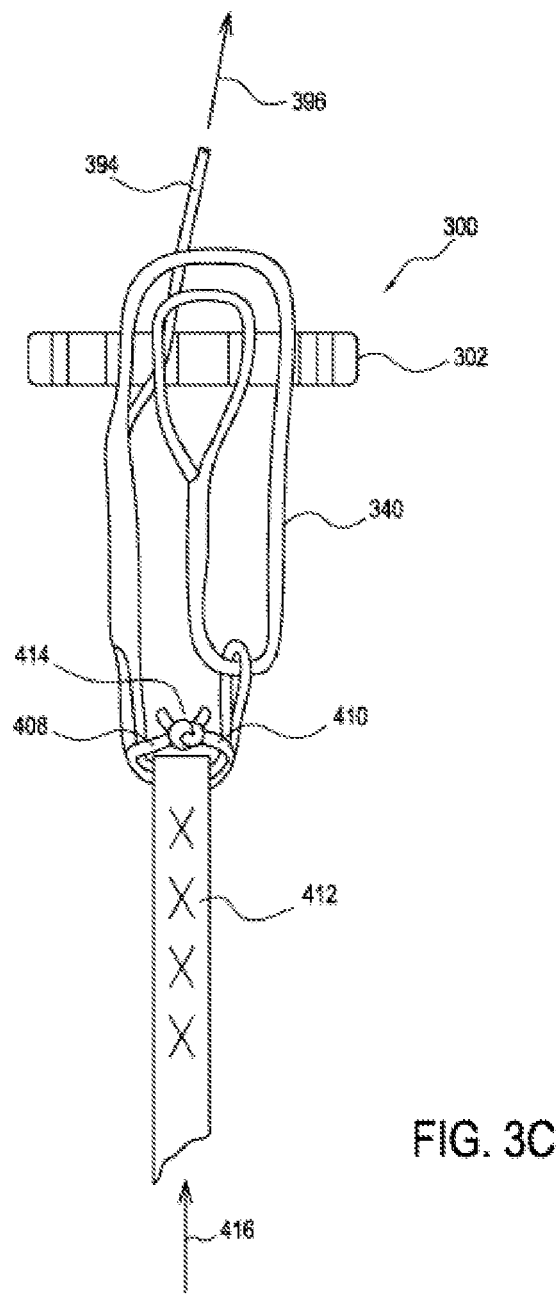
FIG. 3C shows a still further aspect of an adjustable fixation device including a cleat and a suture according to principles of the invention.

FIG. 3C shows a further aspect of the invention in which the tails 408 and 410 of fixation device 300 are secured about a graft 412, with a knot 414 thereby securing the graft 412 to the fixation device 300. Once thus secured, and consistent with the discussion above, position and tension of the graft with respect to cleat 302 and along axis 416 can be adjusted by pulling 396 on tail 394 of suture 340.

FIGS. 4-26 show, in schematic perspective view, selected steps in an exemplary method for preparation of one embodiment of a fixation device 500 according to principles of the invention. Prior to beginning assembly, a length of suture is marked and precut as follows. A temporary holding cleat is fastened to one end of a length of suture. This holding cleat facilitates construction and will be removed upon completion of assembly.

Figure 4:
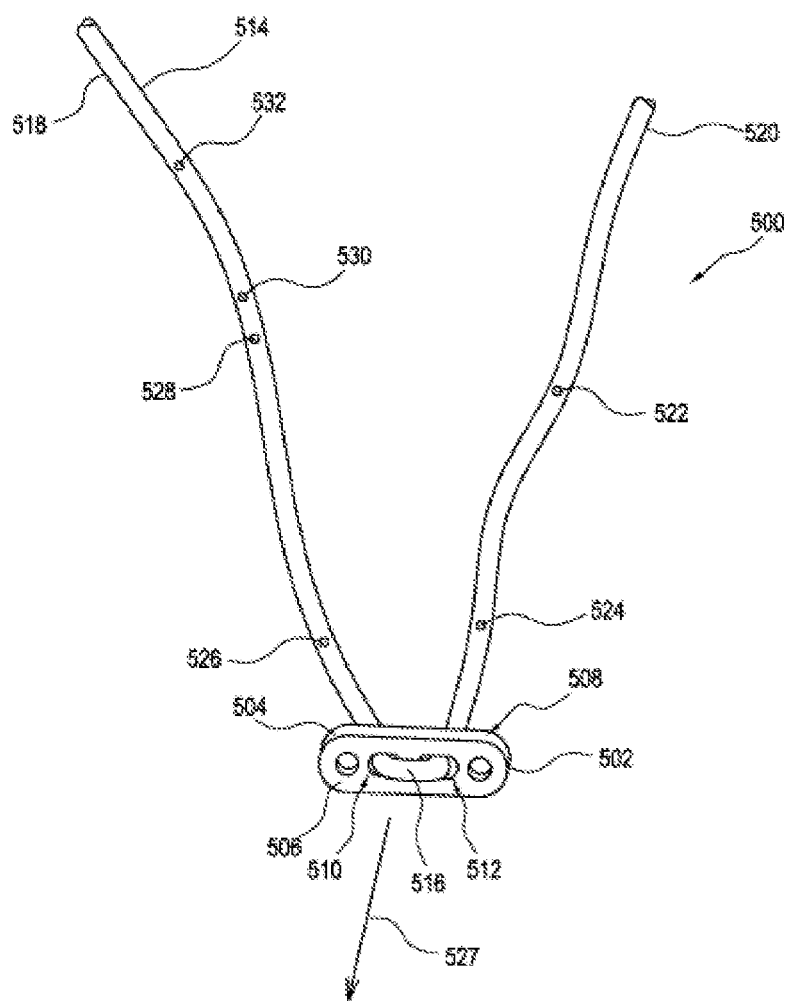
FIGS. 4-25 show, in schematic perspective view, selected steps in an exemplary method for preparation of an adjustable fixation device including a cleat and a suture according to principles of the invention.

FIG. 4 shows a cleat 502 bearing a general similarity to cleat 302 described above. The cleat 502 includes a body member 504 with an outer surface 506, an inner surface 508, a tapered flat oval aperture 510 and a flat oval aperture 512. A length of suture 514 is disposed from an inner side 508 toward the outer side 506 through the tapered flat oval aperture 510, forming a U-shaped bend 516 and passing through the flat oval aperture 512 to return to the inner side 508 of the cleat 502. Defining the two ends of the suture 514 as first end 518 and second end 520, six marks are placed on the suture as follows:

Mark 1—cut at this point to ensure proper length-of-taper in the eye-splice
Mark 2—the second cross of the eye-splice
Mark 3—the first cross of the eye-splice, locks in conjunction with Mark 2
Mark 4—used to align the suture so as to ensure proper loop length
Mark 5—"splice in" where a tail enters the adjustable splice (below "splice out")
Mark 6—"splice out" where the tail exits the adjustable splice In certain embodiments of the invention, Mark 1 will be placed at 0 mm, Mark 2 at 19 mm, Mark 3 at 44 mm, Mark 4 at 70 mm, Mark 5 at 78 mm, Mark 6 at 92 mm. In other exemplary embodiments of the invention, Mark 1 will be placed at 0 mm, Mark 2 will be placed at 15 mm, Mark 3 will be placed at 36 mm, Mark 4 will be placed at 56 mm, Mark 5 will be placed at 58 mm, Mark 6 will be placed at 71 mm. One of skill in the art will appreciate that these dimensions are merely exemplary of a wide variety of different measurements and ratios that will be employed in respective embodiments according to the requirements of particular circumstances.

Referring again to FIG. 4 one sees on suture 514 the placement of Mark 1 522, Mark 2 524, Mark 3 526, Mark 4 528, Mark 5 530, and Mark 6 532. In practicing the method, one pulls the marked end of the suture through the tapered flat oval aperture (hereinafter tapered hole) 510 first and thereafter through the flat oval aperture (hereinafter symmetric hole) 512. The cleat is then centered between Mark 2 524 and Mark 3 526, and the marked side of the suture is facing outward 527.

Figure 5:
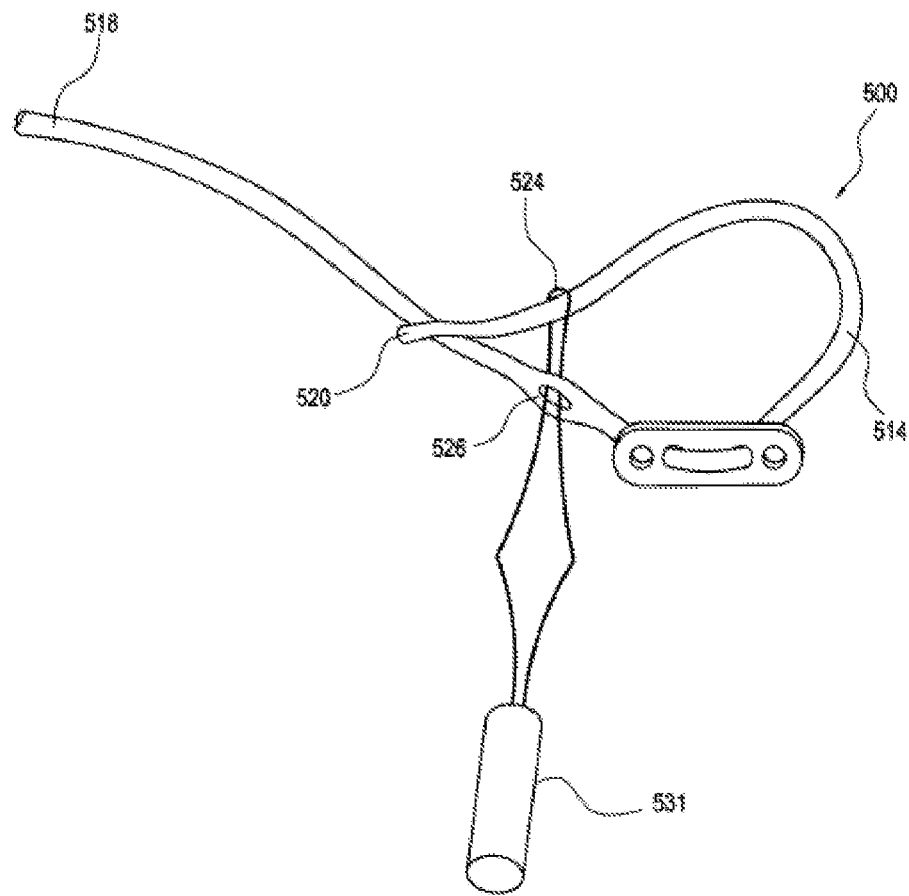

FIG. 5 shows the preparation of fixation device 500 and the use of a suture passer 531 disposed through an aperture at Mark 3 526 and coupled at a distal end thereof to suture 514 at Mark 2 524. Thereafter, the suture passer 531 is withdrawn to bring the suture end through and place the device 500 into the state of FIG. 6.

Figure 6:
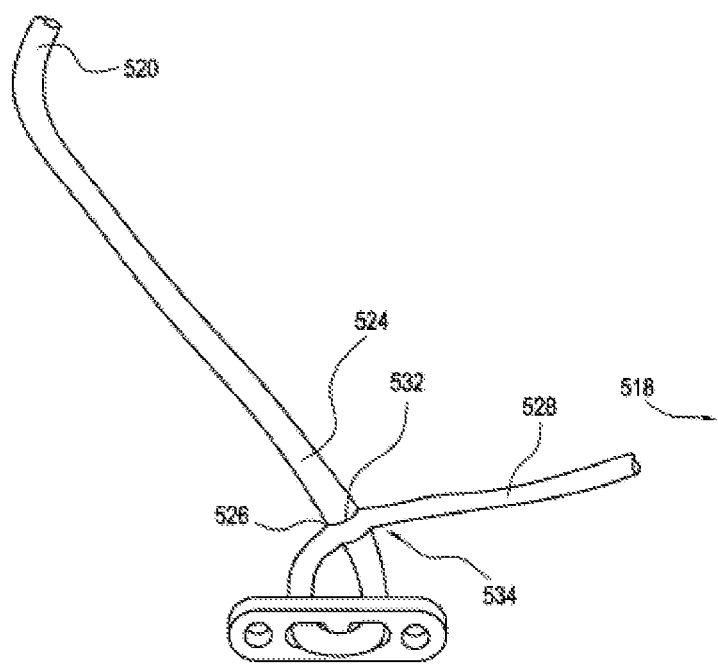

FIG. 6 shows the resulting configuration in which a suture portion 532 is disposed within and transverse to suture portion 534, having passed through an aperture at Mark 3 526. The location of Mark 2 524 is visible.

Figure 7:
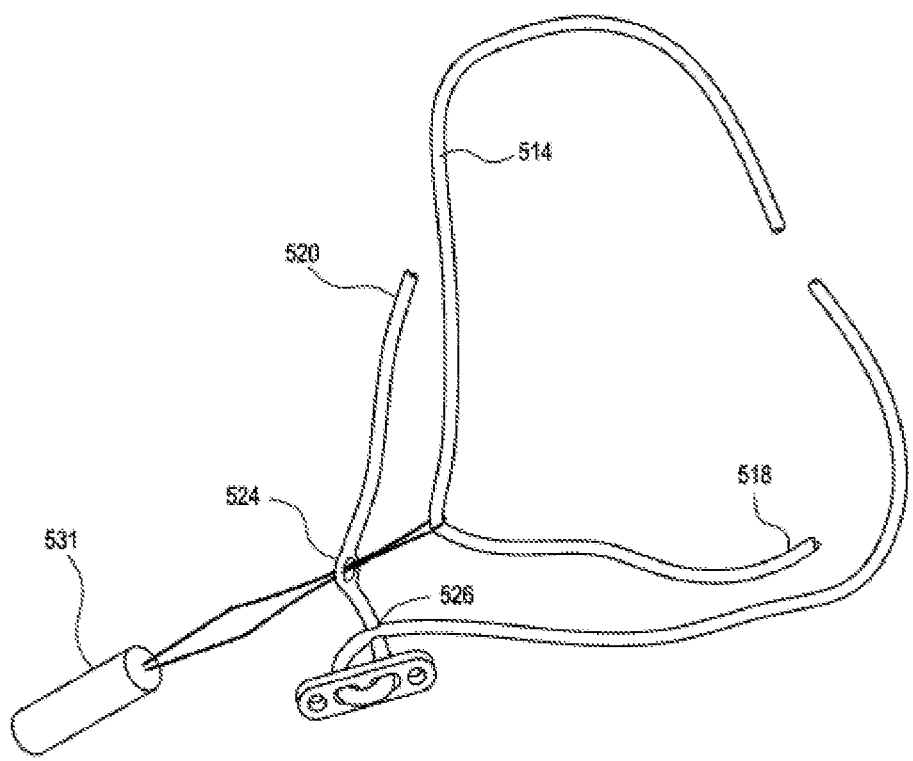

FIG. 7 shows a further step of the method in which suture passer 531 is disposed through an aperture at Mark 2 524 and coupled to suture 514 as shown. The suture passer 531 is then withdrawn to bring suture end 518 through the aperture at Mark 2 524.

Figure 8:
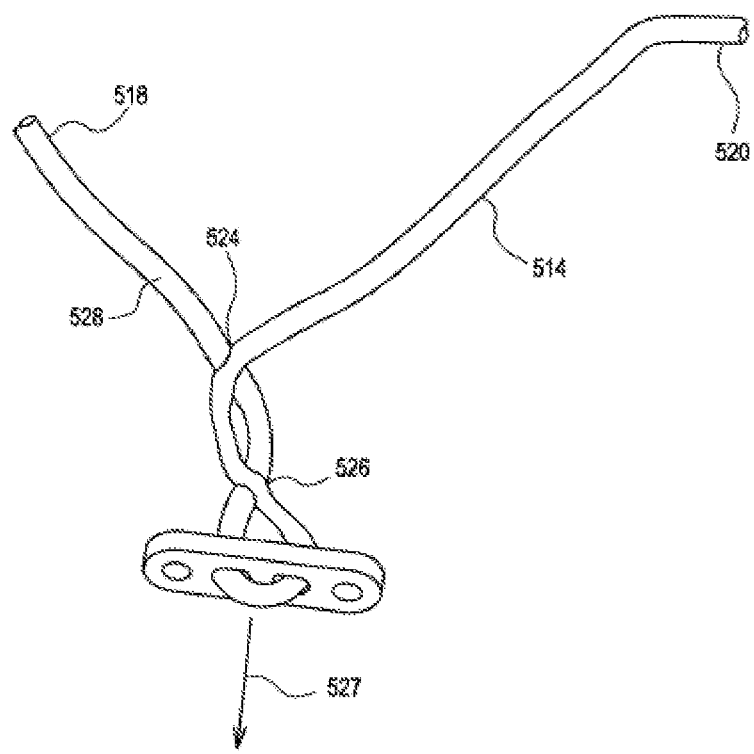

The result is as shown in FIG. 8. The marked side of the suture should continue to face outward 527. Thereafter, the cleat is moved in direction 527 while holding end 518 of the suture 514. This tends to bring the two apertures 526 and 524 towards each other and cinch the splice in place.

Figure 9:
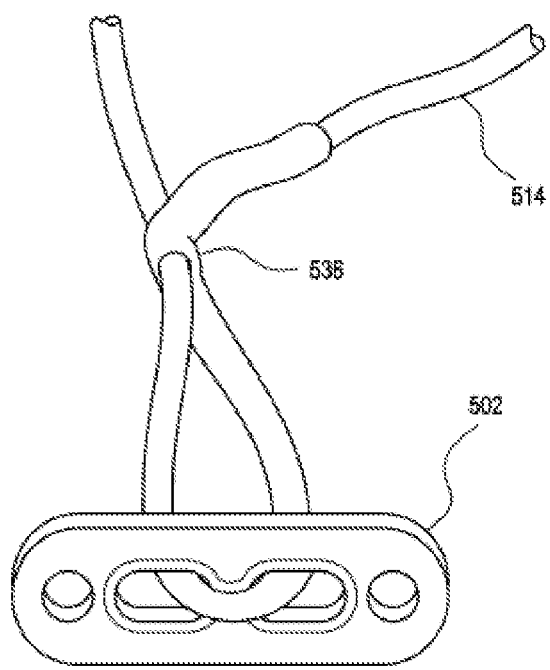

FIG. 9 shows the configuration of the cleat 502 and suture 514 once the splice has been cinched at 536.

Figure 10:
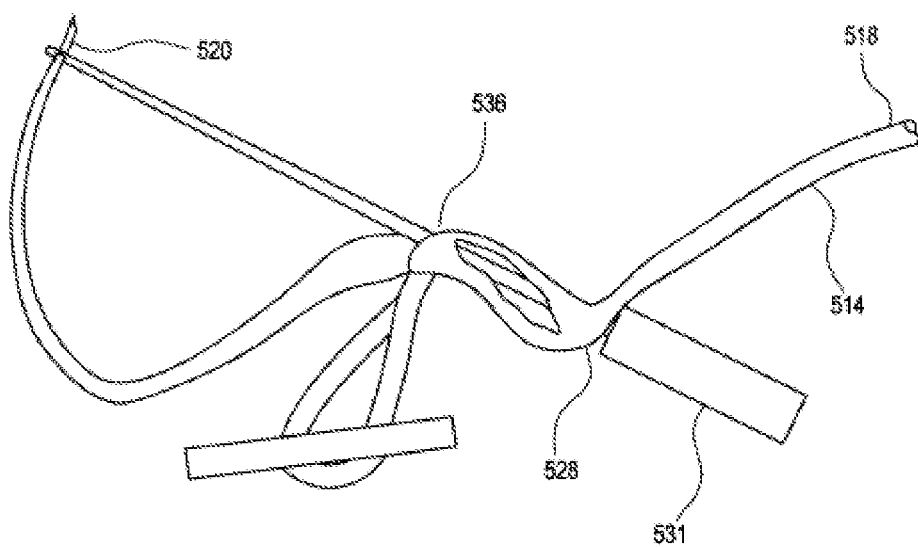

As shown in FIG. 10 the suture passer 531 is then inserted into suture 514 at Mark 4 528, passed axially within the suture and out of the suture as close as possible to location 536. The suture passer 531 is then coupled to end 520 of suture 514 and withdrawn, bringing end 520 of the suture back through location 536 and out at Mark 4 528.

Figure 11:
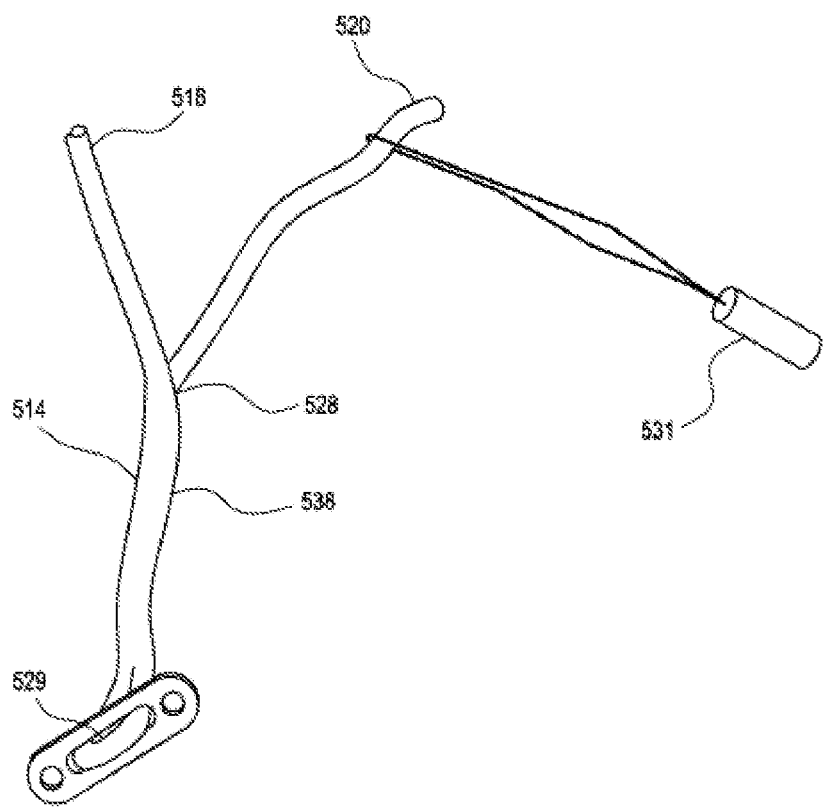

FIG. 11 shows a result with end 520 of suture 514 having been pulled axially through the splice at 538. The balance of suture 514 towards end 520 is then cut off in close proximity to where it emerges at 528. A mark is made 529 at the center of the eye splice loop on the suture facing the upper surface 506 of the cleat 502.

Figure 12:
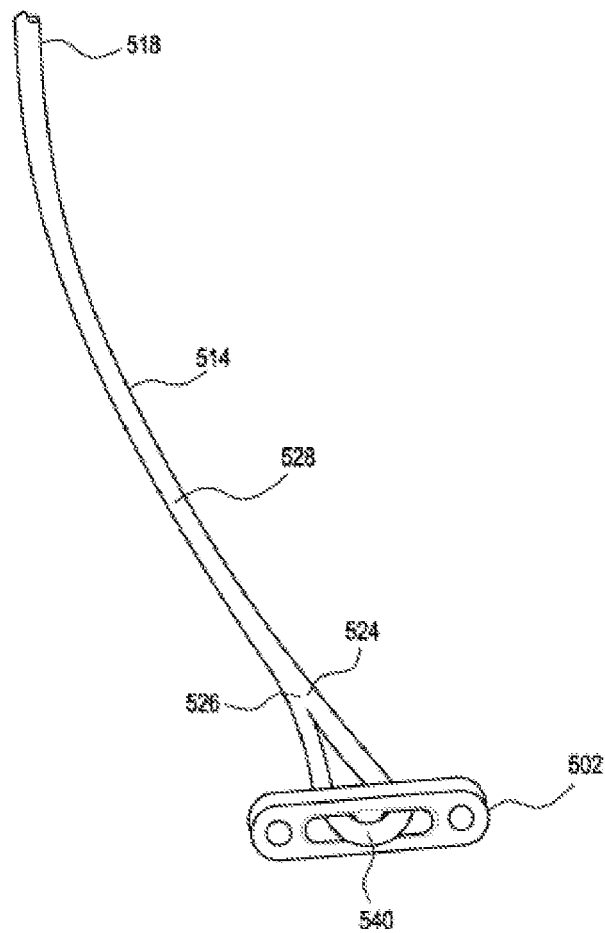

The result, as shown in FIG. 12 is a single end 518 of the suture 514, coupled with an eye-splice loop 540 to the cleat 502. At this point, a quality check will ensure that the suture is not frayed, that the eye-splice ends are substantially coincident with Mark 2 524 and with Mark 3 526, that the transverse passages of the suture through the suture body are centered and symmetrical, and that the suture is not unduly twisted. In addition, it should be confirmed that the coaxial internal portion of the suture, previously coupled to end 520, terminates short of Mark 4 528 and that the tail of this coaxial internal portion is completely within the outer suture.

Figure 13:
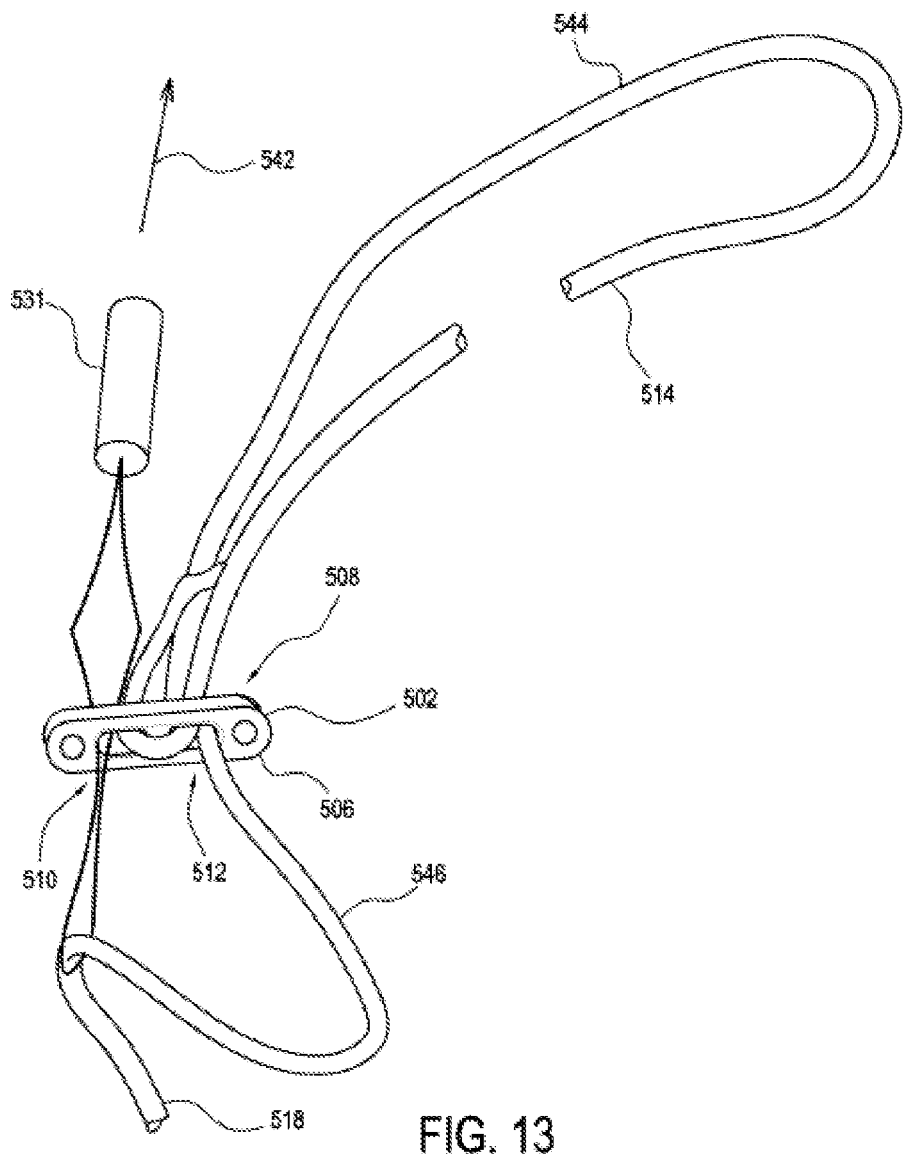

In a further step of the method, suture passer 531 is disposed through the symmetric hole 512 from the upper surface 506 towards a lower surface 508 of the cleat 502. End 518 of suture 514 is coupled to a distal end of the suture passer 531. The suture passer 531 is withdrawn bringing end 518 of suture 514 through the upper surface of the cleat 502. Thereafter, and as shown in FIG. 13, suture passer 531 is passed through tapered hole 510 of cleat 502 from the lower surface 508 towards the upper surface 506. A distal end of the suture passer 531 is coupled to suture 514 near its end 518. The suture passer is then withdrawn 542, bringing end 518 through tapered hole 510 and out on the lower surface 508 side of the cleat 502. This forms a loop 544 of suture 514 at the lower surface 508 of cleat 502 and a further loop 546 of suture 514 at the upper surface 506 of cleat 502.

Figure 14:
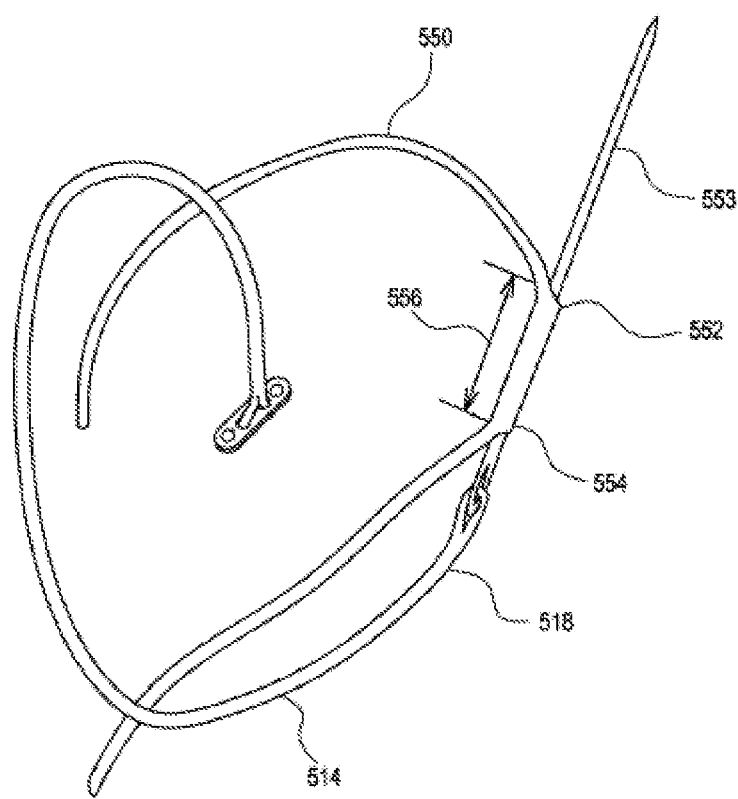

FIG. 14 illustrates the method steps involved in preparing a sleeve for a fixation device 500 according to principles of the invention. A length of suture 550 is marked at symmetrically intermediate points 552, 554 to define a length of suture 556 therebetween. One of skill in the art will understand that length 556 is selected according to the requirements of a graft to performed, and is related to a width of the graft tissue.

A point of a suture shuttle 553 is inserted at 554 and passed coaxially within the suture to 552, where the suture shuttle 553 point emerges from the suture. The suture shuttle is used to draw end 518 of suture 514 (as previously described above) through the suture 550.

Figure 15:
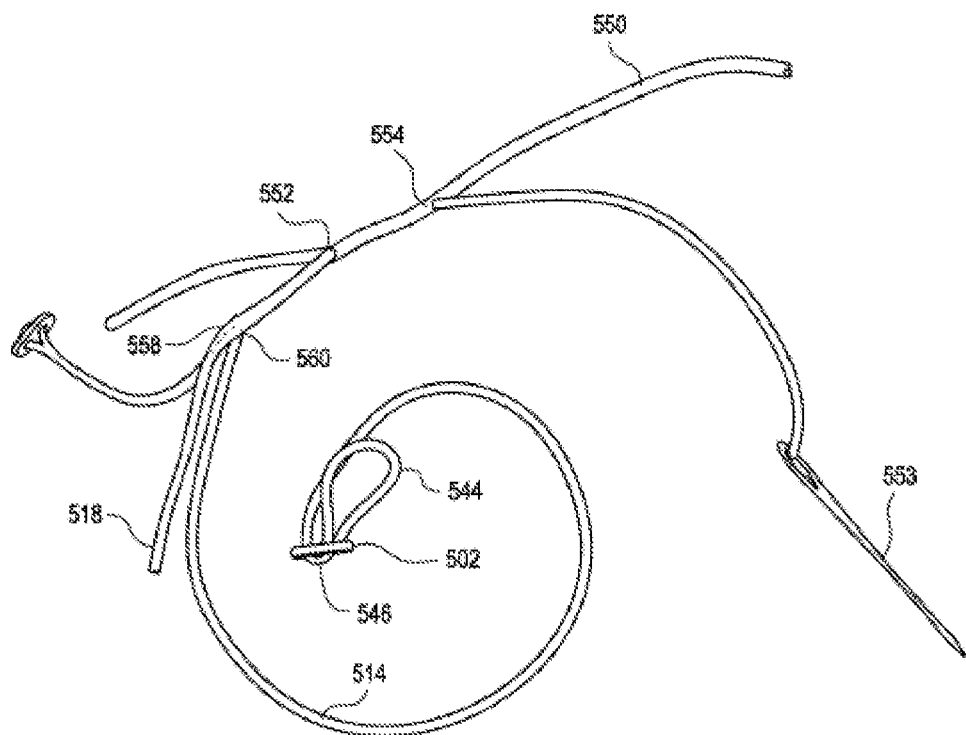

FIG. 15 shows cleat 502 including suture loop 544 and suture loop 546 as discussed in relation to FIG. 13. Also visible is end 518 of suture 514 coupled to a loop 558 of the suture shuttle 553 at an intermediate point 560 of suture 514. The suture shuttle 553 is being used to draw end 518 of suture 514 through the suture (sleeve) 550 between points 552 and 554.

Figure 16:
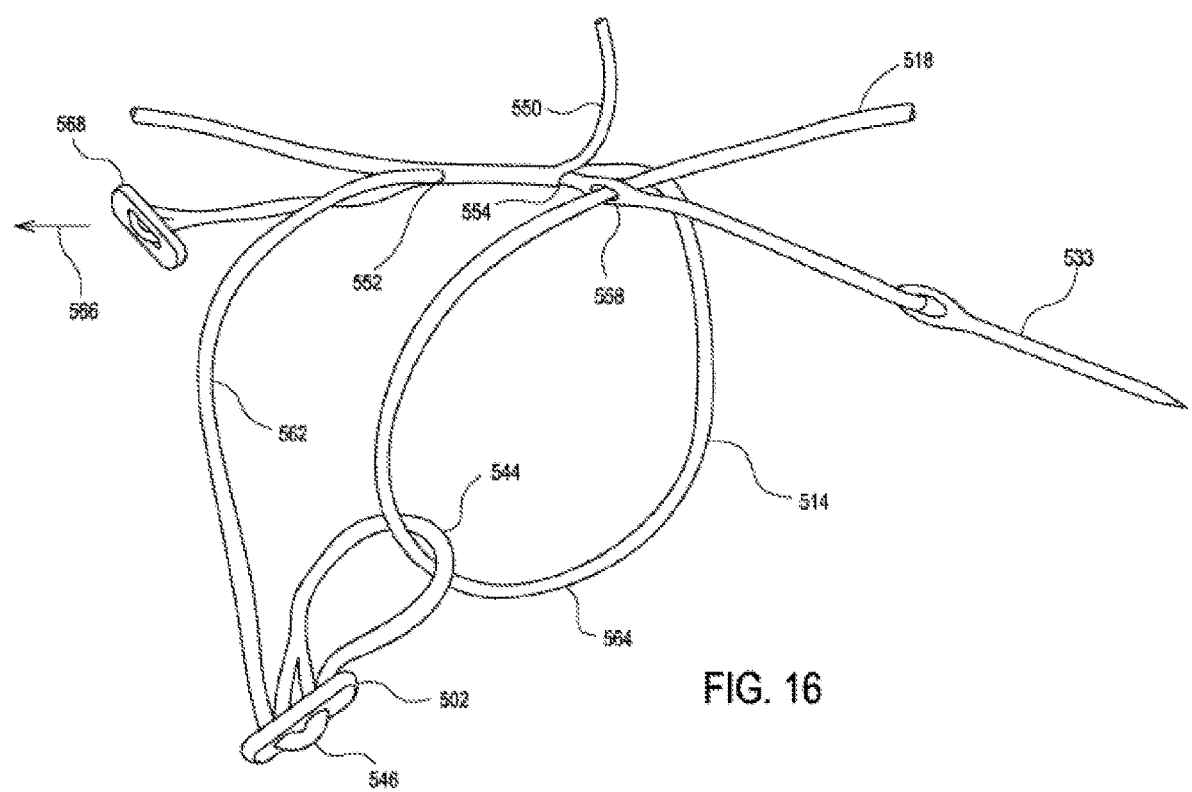

FIG. 16 shows a further step in the method of preparing a fixation device 500. As is evident from the figure, suture 514 is looped from the eye splice through loop 544 and passes through cleat 502 to form loop 546 at the upper surface of cleat 502. Thereafter it passes through cleat 502 again past the lower surface where it proceeds as suture portion 562, entering the sleeve at point 552 and exiting at point 554. Suture 514 then forms a further loop at portion 564, passing through loop 544 and thereafter passing through loop 558 of the suture shuttle 553. Thereafter, tension is applied 566 to a terminal cleat 568 of the suture shuttle, drawing end 518 of suture 514 back into sleeve 550 at point 554 and out again at point 552.

Figure 17:
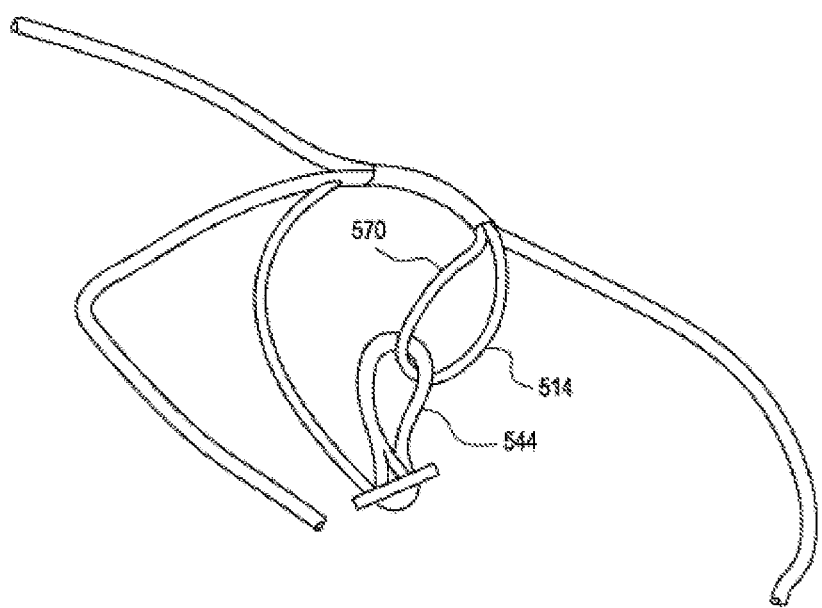

FIG. 17 shows a result, where portion 564 of suture 514 forms and interlinked loop 570 with loop 544.

Figure 18:
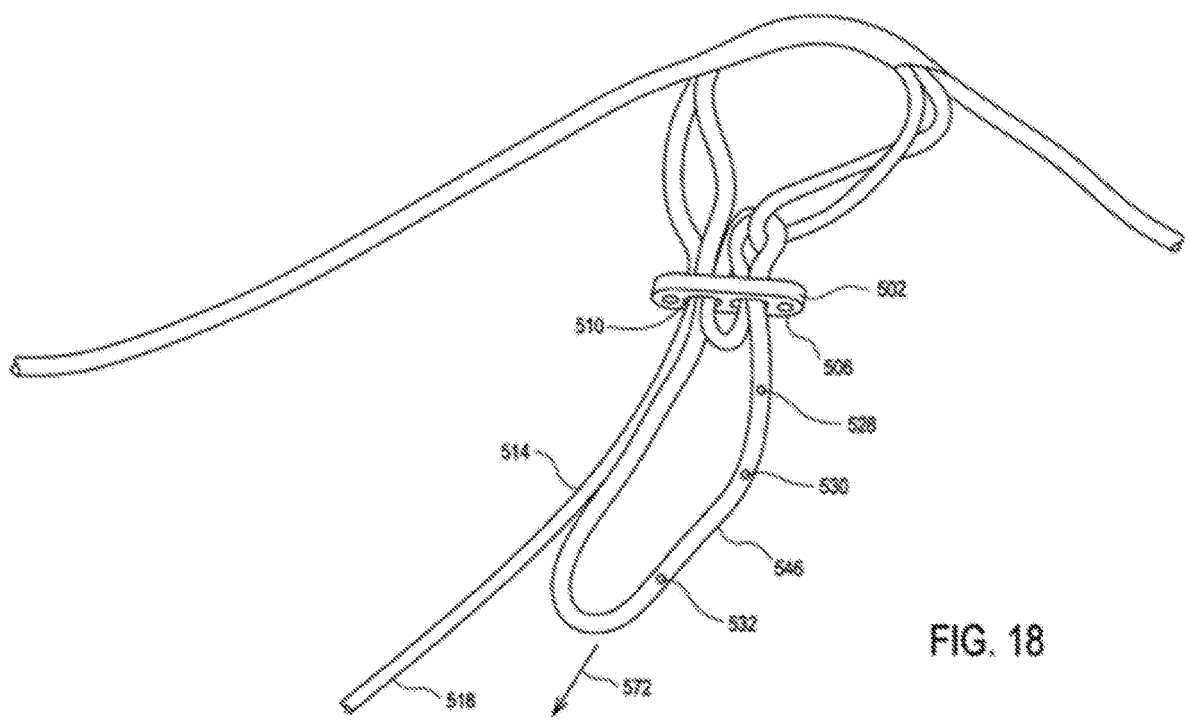

FIG. 18 shows a further step in the method of forming a fixation device 500. Specifically, end 518 of suture 514 is drawn through tapered hole 510 from the inner side 508 towards the outer side 506 of cleat 502 with the suture passer (not shown). Tension is then applied to previously identified loop 546 to draw suture 514 through the cleat 502 and expand loop 546. The loop is expanded until Mark 4 528, Mark 5 530 and Mark 6 532 are at the upper surface 506 side of the cleat 502.

Figure 19:
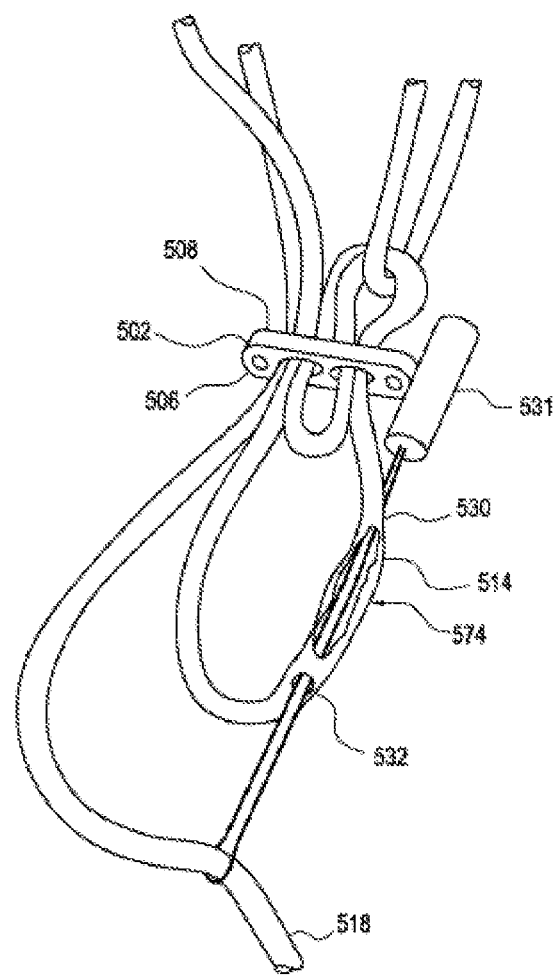

FIG. 19 shows a further step in the method of forming a fixation device 500. In this step, suture passer 531 is inserted into suture 514 at the opposite side of the suture from Mark 5 530, passed coaxially within the suture of loop 546, and passed out of suture 514 at Mark 6 532 on the same side of suture 514 as Mark 6. End 518 of suture 514 is coupled to the distal end of suture passer 531 and drawn back into the suture at Mark 6 532, through the suture 514 coaxially and back out of the suture at 530, thus forming an adjustable splice 574, as further shown in FIG. 20.

Figure 20:
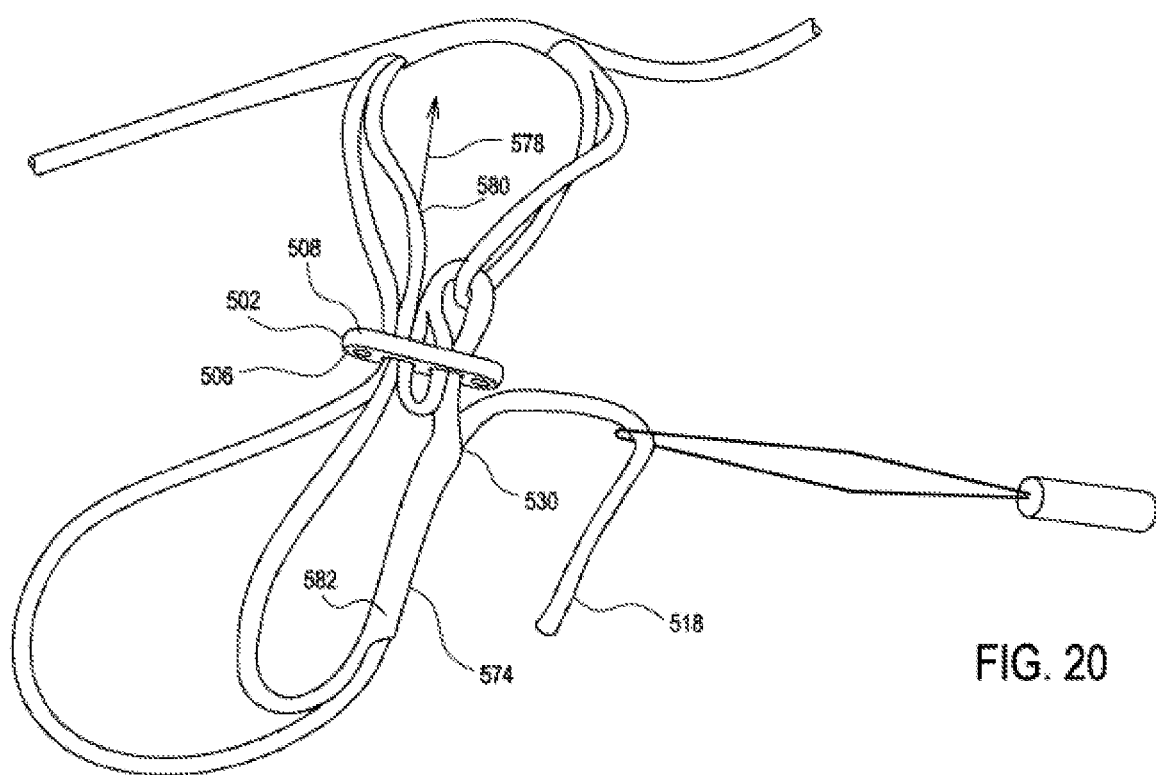

Referring further to FIG. 20, tension 578 is applied to suture 514 at region 580 and the portion 582 of adjustable splice 574 is drawn through cleat 502 from upper surface 506 towards lower surface 508 so as to transfer portion 582 of the adjustable splice 574 to the lower surface side of the cleat.

Figure 21:
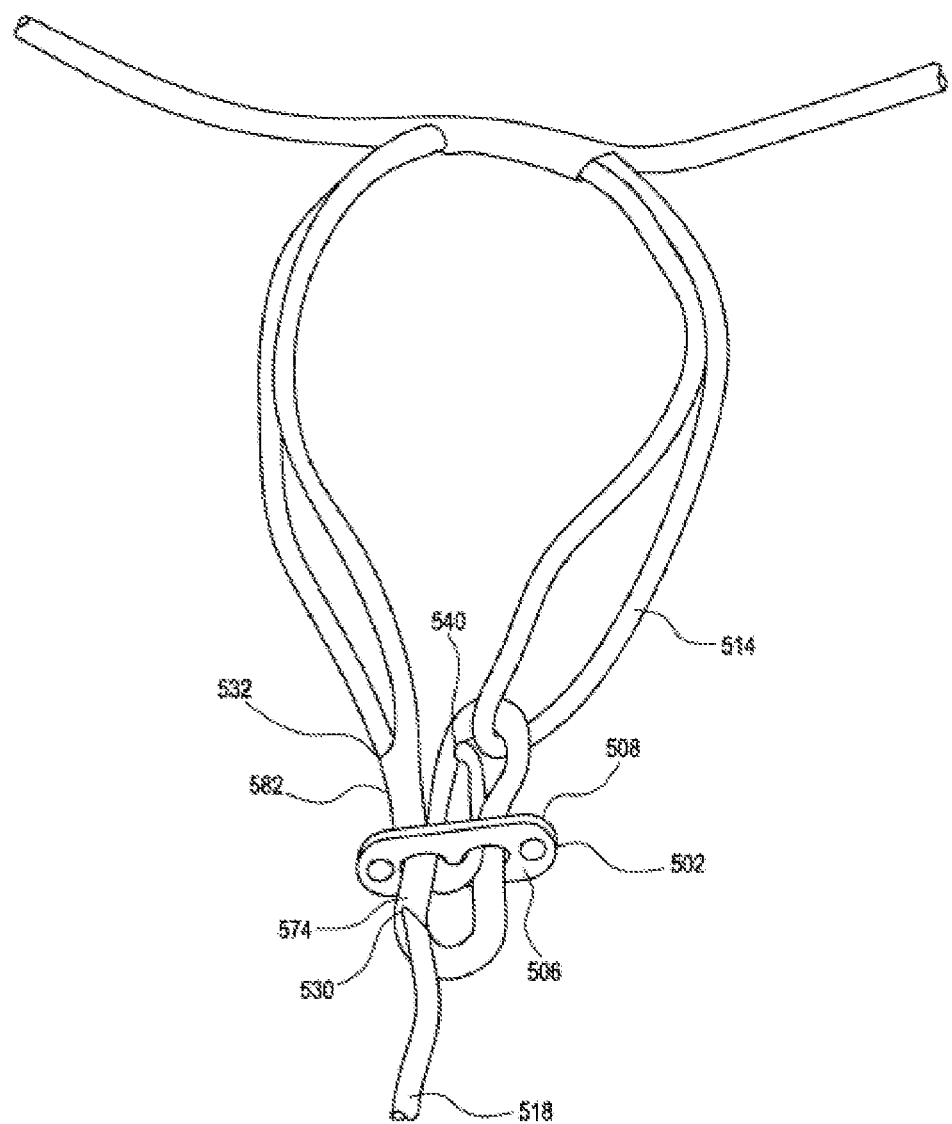

This result is visible in FIG. 21 where and 518 of suture 514 emerges from the adjustable splice at Mark 6 532 at the outer surface 506 side of cleat 502 while a further portion 582 of the adjustable splice 574 is disposed beyond the inner surface 508 of cleat 502.

In certain embodiments, the method of preparing fixation device 500 now includes the steps of ensuring that no fraying of the sutures has happened, especially around the adjustable splice and sleeve, the assembly is inspected to ensure that the suture has run properly through the cleat. After the eye-splice loop 540, the suture 514 should run into the symmetric hole 512 first, and thereafter into the tapered hole 510. End 518 of suture 514 should exit the adjustable splice 574 on the same side of cleat 502 as upper surface 506. The suture should enter the adjustable splice on the same side as, and directly through, Mark 6 532 and exit the adjustable splice on the opposite side of the suture 514 from Mark 5 530. The length of the symmetric splice 574 should be equally divided on opposite sides of the cleat 502.

Figure 22:
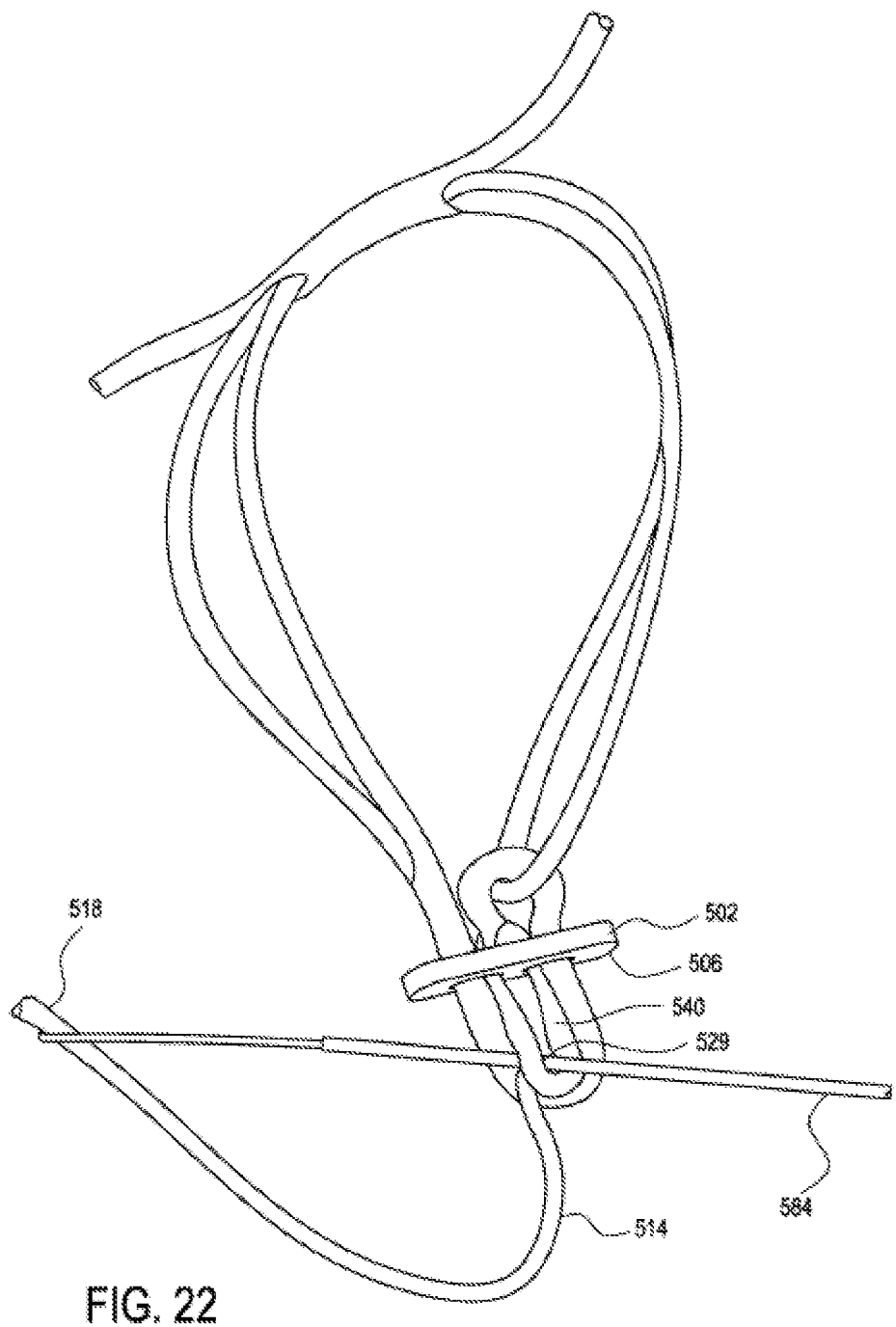

FIG. 22 shows a further step in a method of forming an adjustable fixation device 500 including drawing the eye-splice loop 540 to the upper surface 506 side of cleat 502, passing a needle 584 from an inner surface of the eye-splice loop through the mark at 529 made and described in relation to FIG. 11. A distal end of the needle 584 is coupled to end 518 of suture 514 and drawn back through the suture from the outside to the inside of the eye-splice loop 540 at the mark 529.

Figure 23:
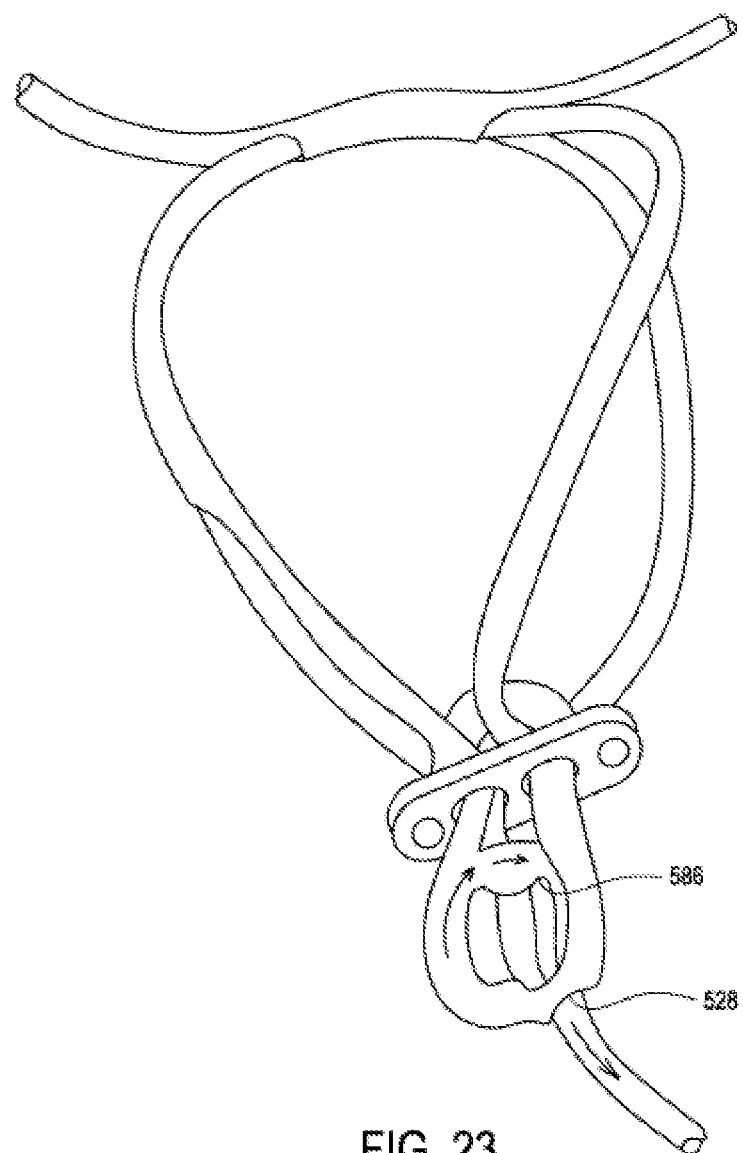

Thereafter, as shown in FIG. 23, the needle 584 is employed to further draw the end 518 of the suture 514 through location 586 at the top of the eye-splice loop 542 and then through the suture 514 at Mark 4 528.

Figure 24:
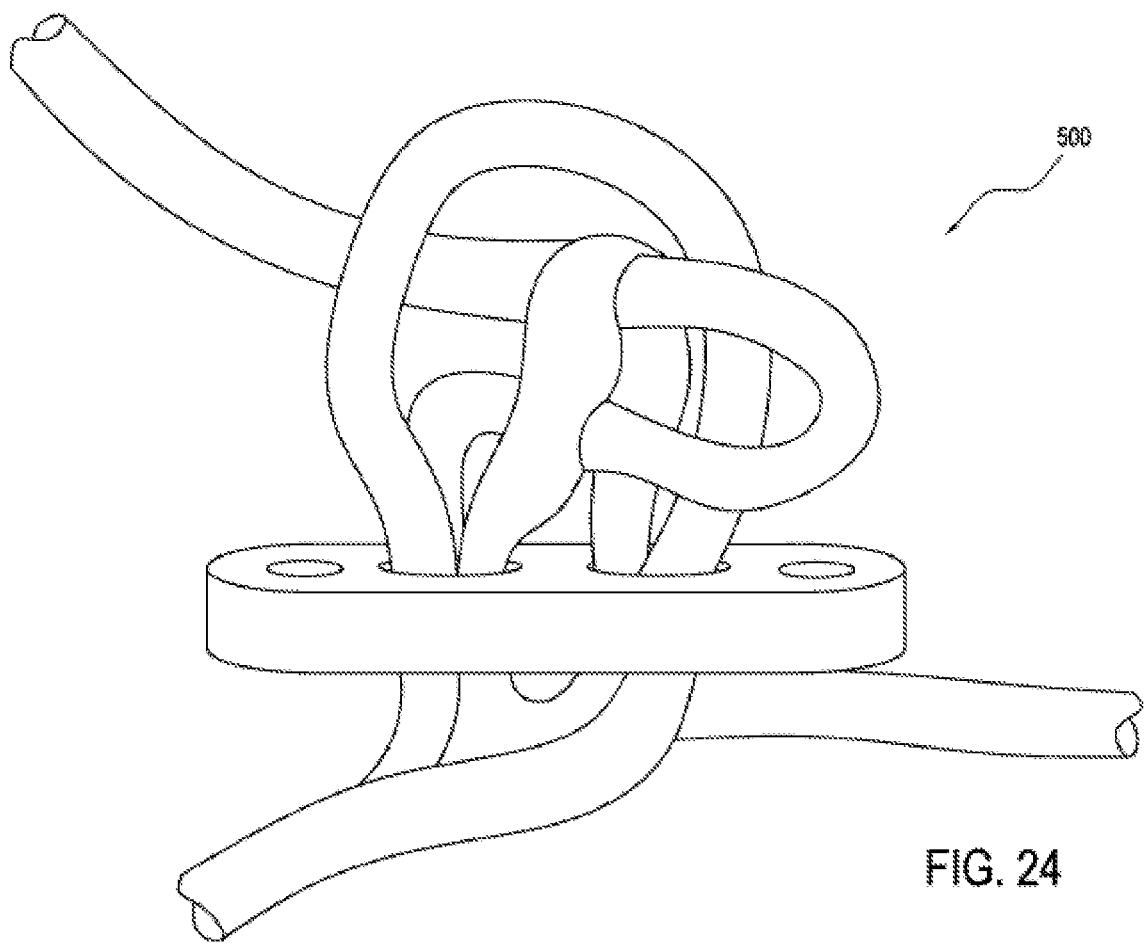
Figure 25:
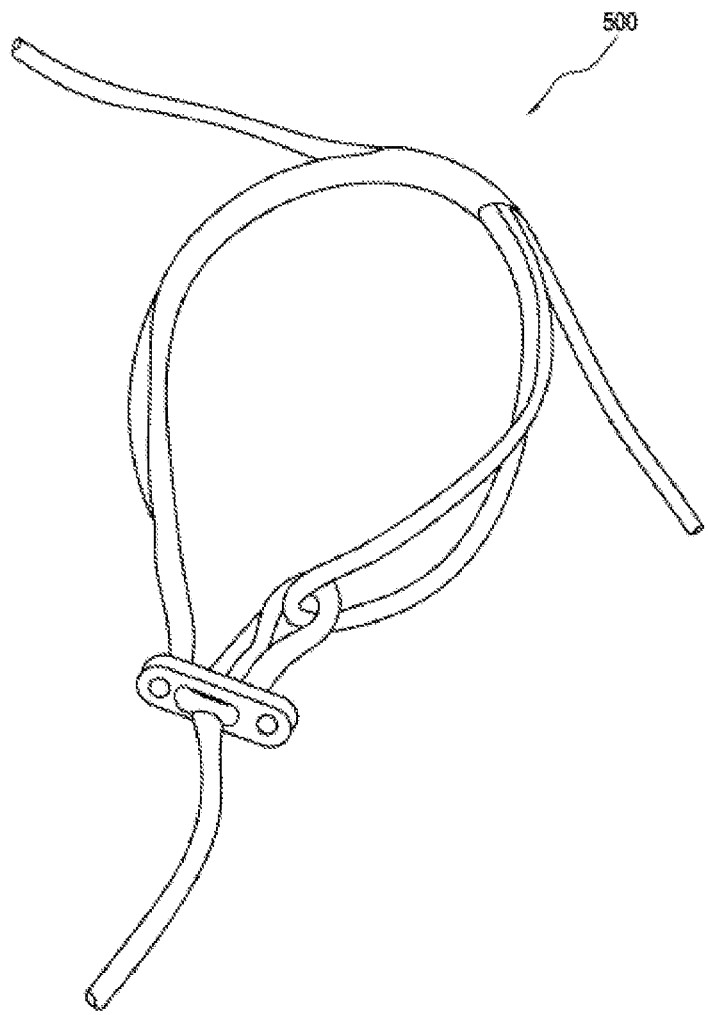

The adjustable fixation device 500 will now be in the configuration illustrated in FIG. 24. The method that includes ensuring that there is no fraying of suture material, ensuring that crosses are properly through the center of the suture and all marks are facing away from the cleat.

Thereafter, to achieve the final configuration the eye splice is lightly pulled towards the lower side 508 of the cleat 502. Thereafter, simultaneously pulling on the eye splice and end 518 of the suture 514 will further finalize positioning of the sutures. The suture is pulled towards the lower side 508 of the cleat 502 at the symmetric whole and that the entire loop is pulled from the bottom working gently to avoid punching. Finally it should be confirmed that the end of the suture 518 moves freely to adjust the size of the graft fixturing loop.

Figure 26:
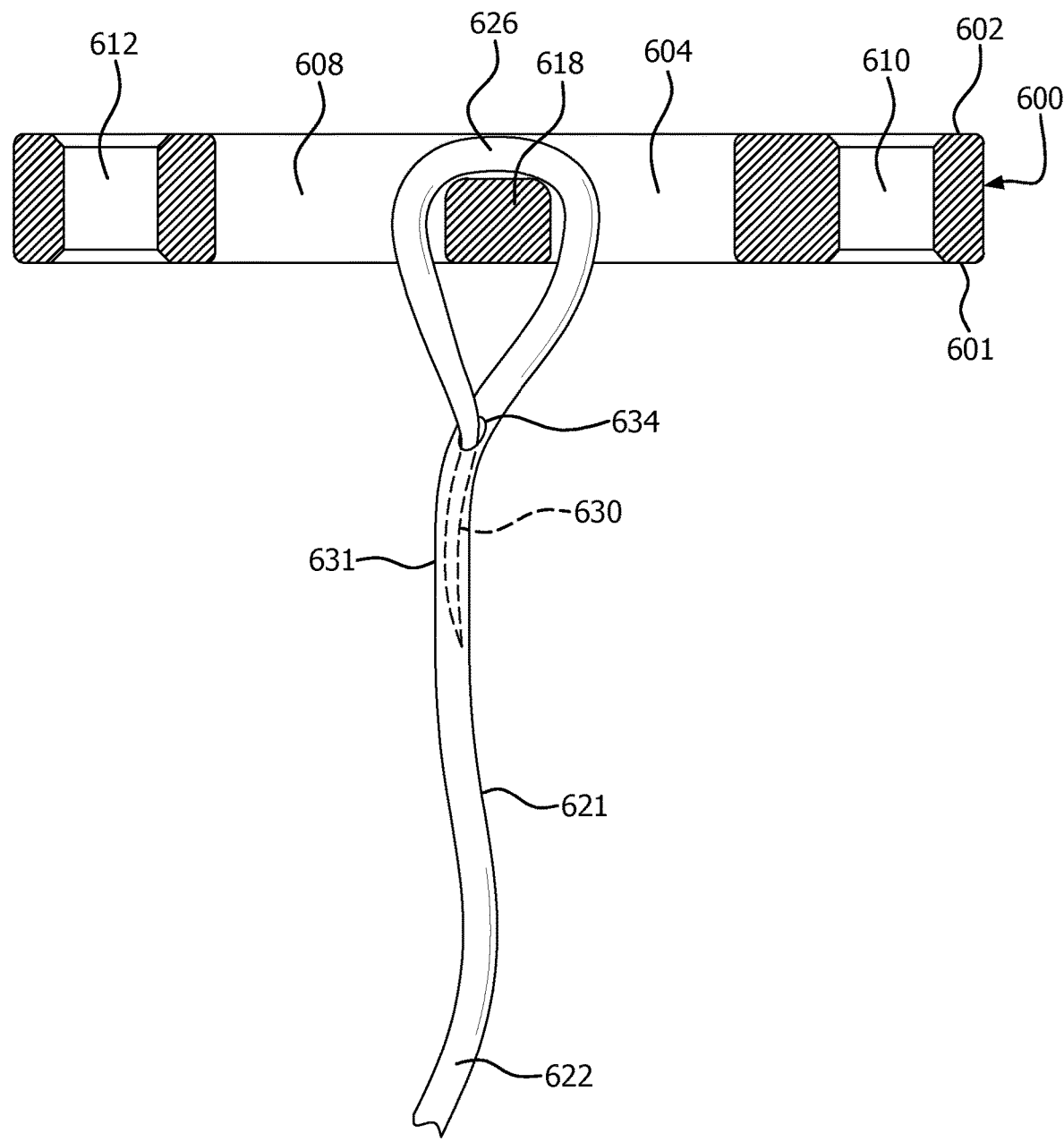
FIG. 26 is a side elevation partially in cross-section and partially in phantom, of an adjustable fixation device in a first stage of assembly.

There is shown in FIGS. 26-30 an illustration of a sequence of steps to create an adjustable fixation device according to one embodiment of the invention. There is shown in FIG. 26 a cleat 600 having a bottom surface 601 and a top surface 602, and an oval bore 604 and a tapered bore 608. The cleat 600 can have circular apertures 610 and 612. A bridge or seat portion 618 spans between the oval bore 604 and the tapered bore 608.

Figure 27:
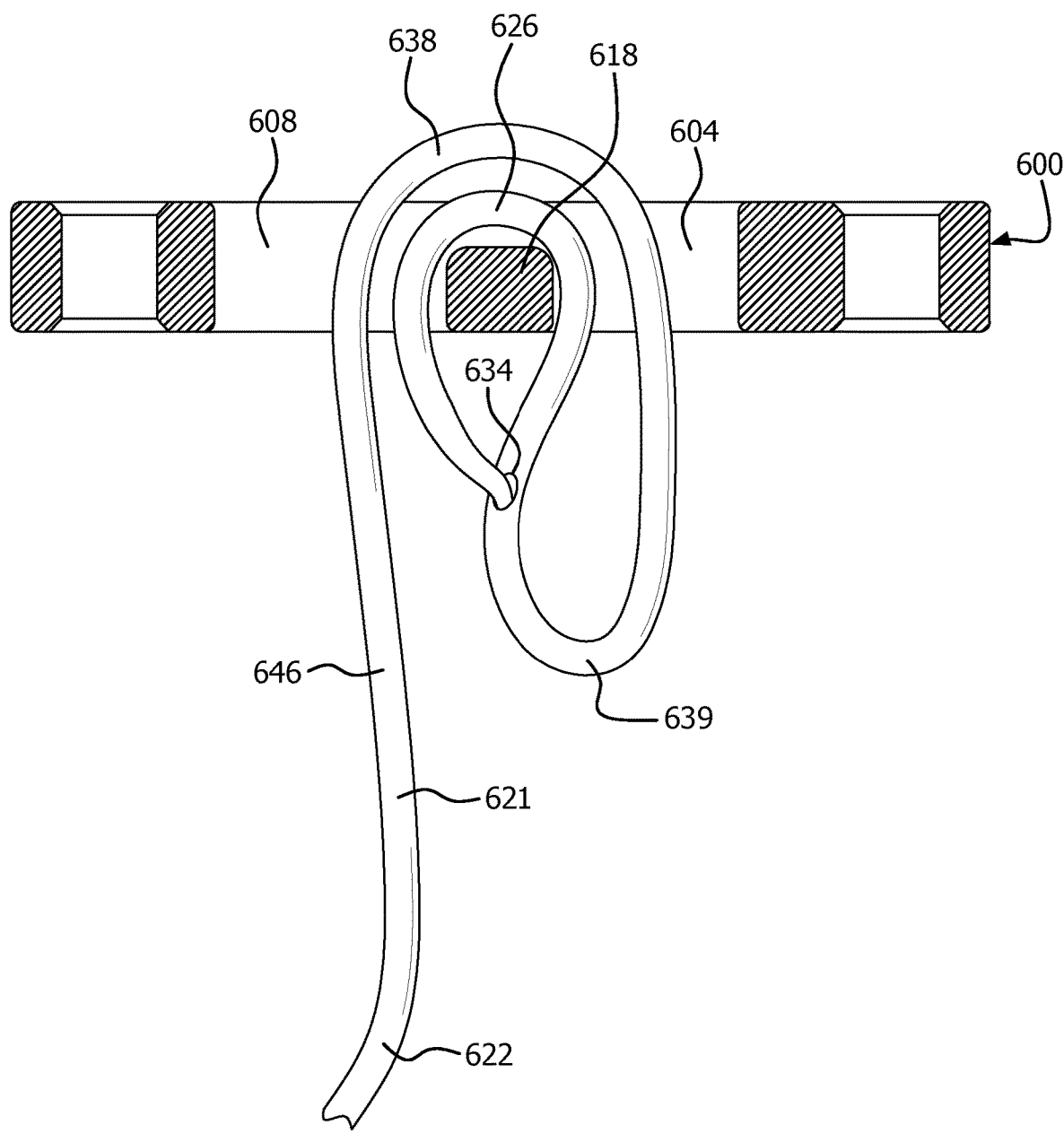
FIG. 27 is a side elevation partially in cross-section of an adjustable fixation device in a second stage of assembly.

A flexible connector 621 has a tail 622 and a portion of the flexible connector 621 passes through the oval bore 604 and over the bridge portion 618 and through the tapered bore 608 to form a downward facing inner bend 626. A first end 630 of the flexible connector 621 is captured longitudinally within a portion 631 of the suture 621 and enters the flexible connector 621 at an aperture 634. As shown in FIG. 27, a downward facing outer bend 638 of the flexible connector 621 is returned to the oval bore 604 forming an upward facing bend 639. A portion 646 of the flexible connector 621 passes through the tapered bore 608 such that the downward facing outer bend portion 638 is over the downward facing inner bend portion 626.

Figure 28:
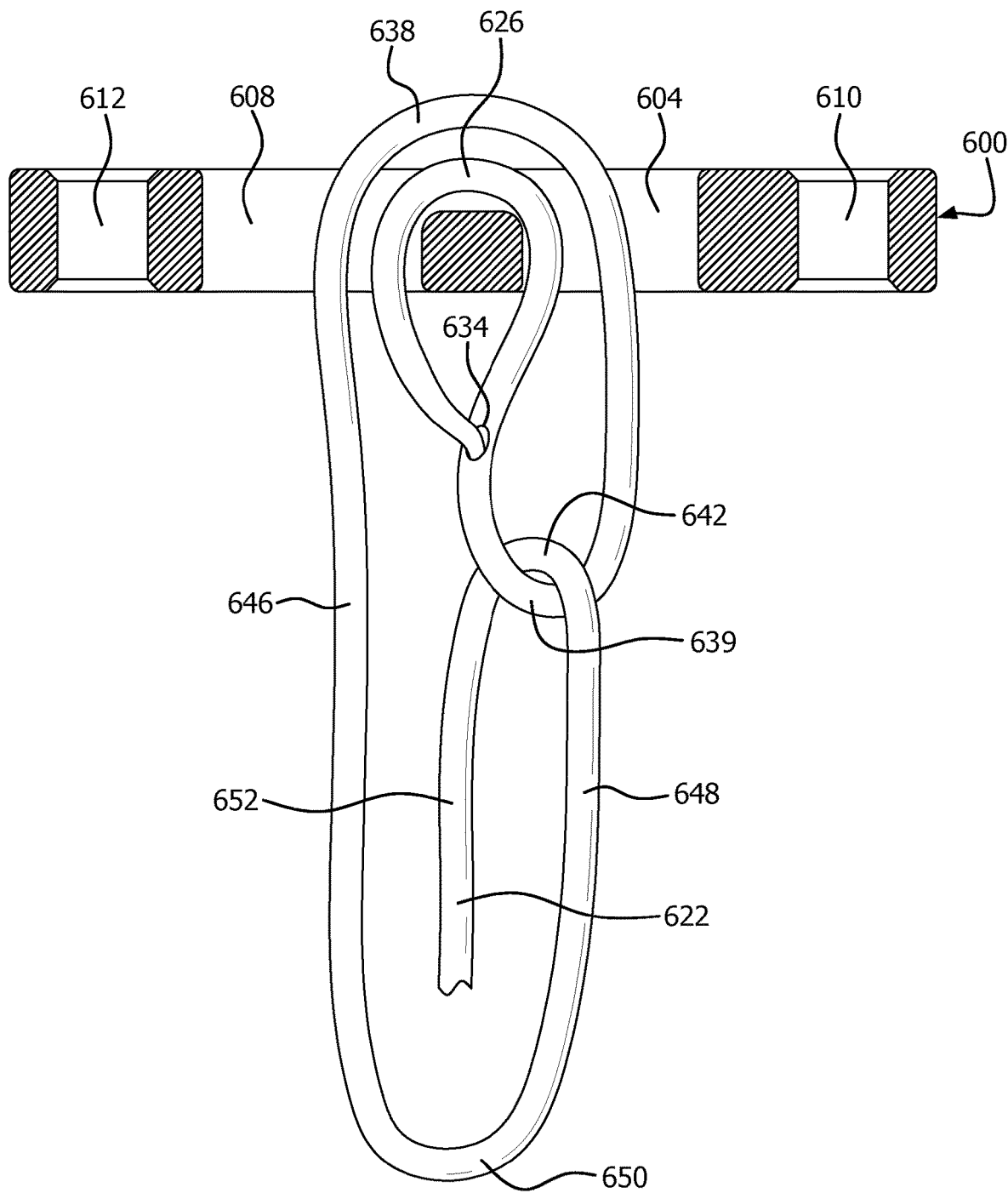
FIG. 28 is a side elevation partially in cross-section of an adjustable fixation device in a third stage of assembly.
Figure 29:
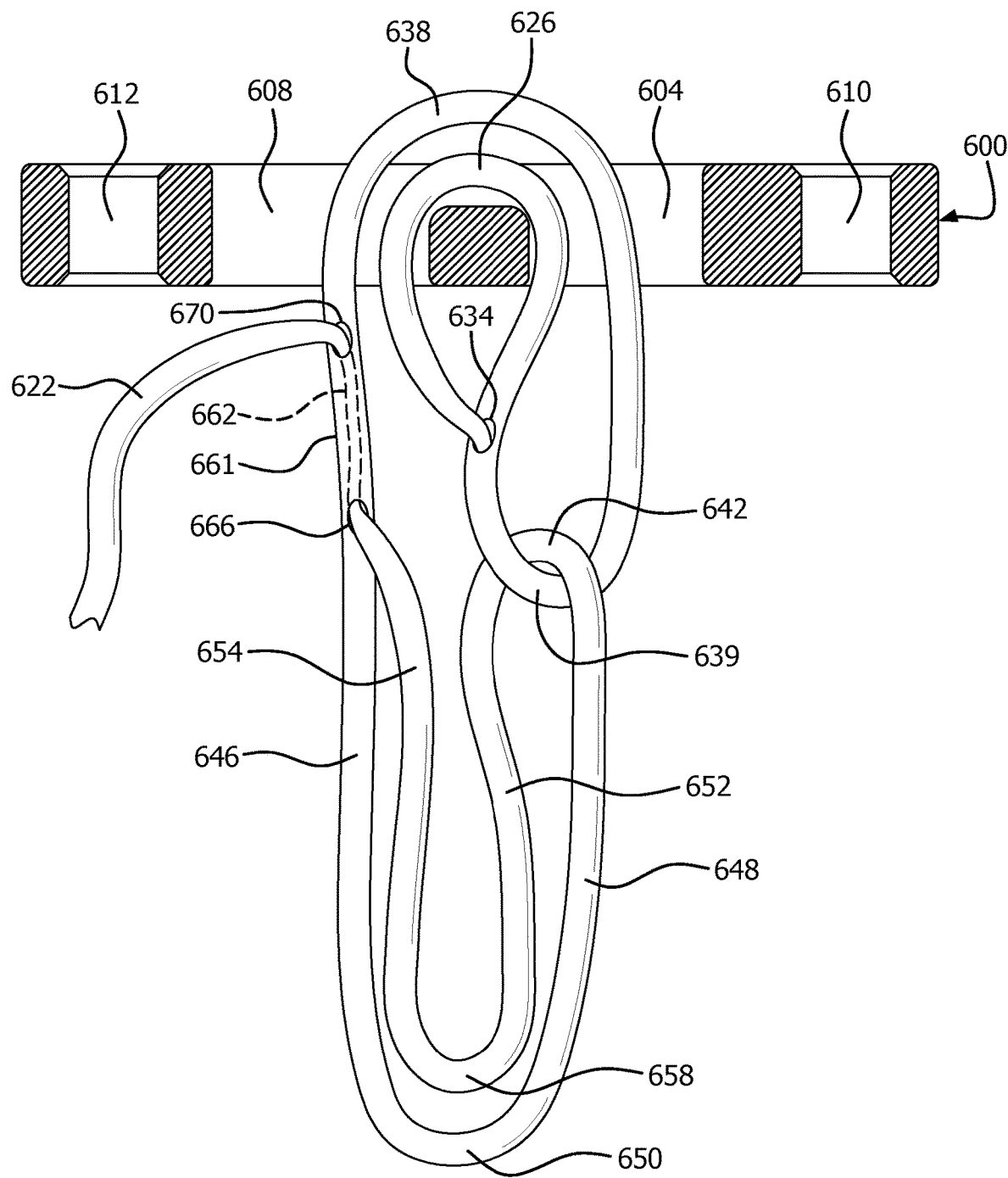
FIG. 29 is a side elevation partially in cross-section and partially in phantom, of an adjustable fixation device in a fourth stage of assembly.

As shown in FIGS. 28-29, the tail 622 can be passed over the upward facing bend 639 to form a downward facing bend 642 that rests on the upward facing bend 639 with an ascending portion 648 and a descending portion 652. An upward facing bend 650 is thereby formed. The descending portion 652 is turned upward at a bend 658 to form an ascending portion 654. A portion 662 of the ascending portion 654 is captured longitudinally within a portion 661 of the portion 646 and enters at an aperture 666 and exits at an aperture 670.

Figure 30:
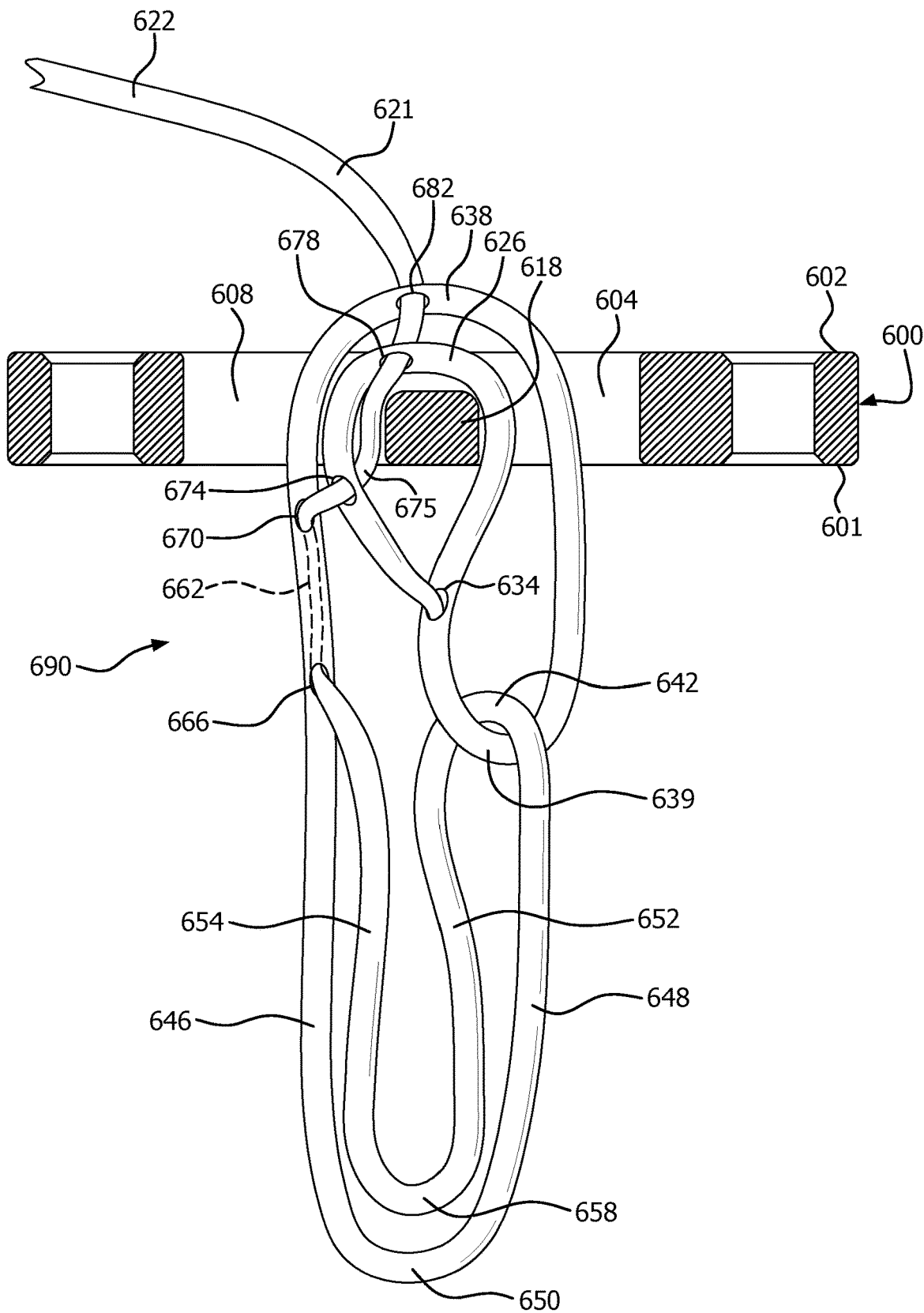
FIG. 30 is a side elevation partially in cross-section and partially in phantom, of an adjustable fixation device in a fifth stage of assembly.

As shown in FIG. 30, upon leaving the aperture 670 the flexible connector 621 transversely engages the downward facing inner bend 626 through an aperture 674 that is below a bottom surface 601 of the cleat 600. A portion 675 of the flexible connector 621 leaving the aperture 674 abuts the bridge portion 618 and is positioned between the bridge portion 618 and a corresponding portion of the downward facing bend 626. The portion 675 transversely enters a portion of the downward facing bend 626 above the seat portion 618 at an aperture 678. The suture 621 then transversely passes through the downward facing outer bend 638 at an aperture 682. The tail 622 extends above the cleat 600 to complete the adjustable fixation flexible connector portion 688 portion and with the cleat 600 the adjustable fixation device 690. The tail 622 will provide tensioning to tension and secure the adjustable fixation device 690 in position.

Figure 31:
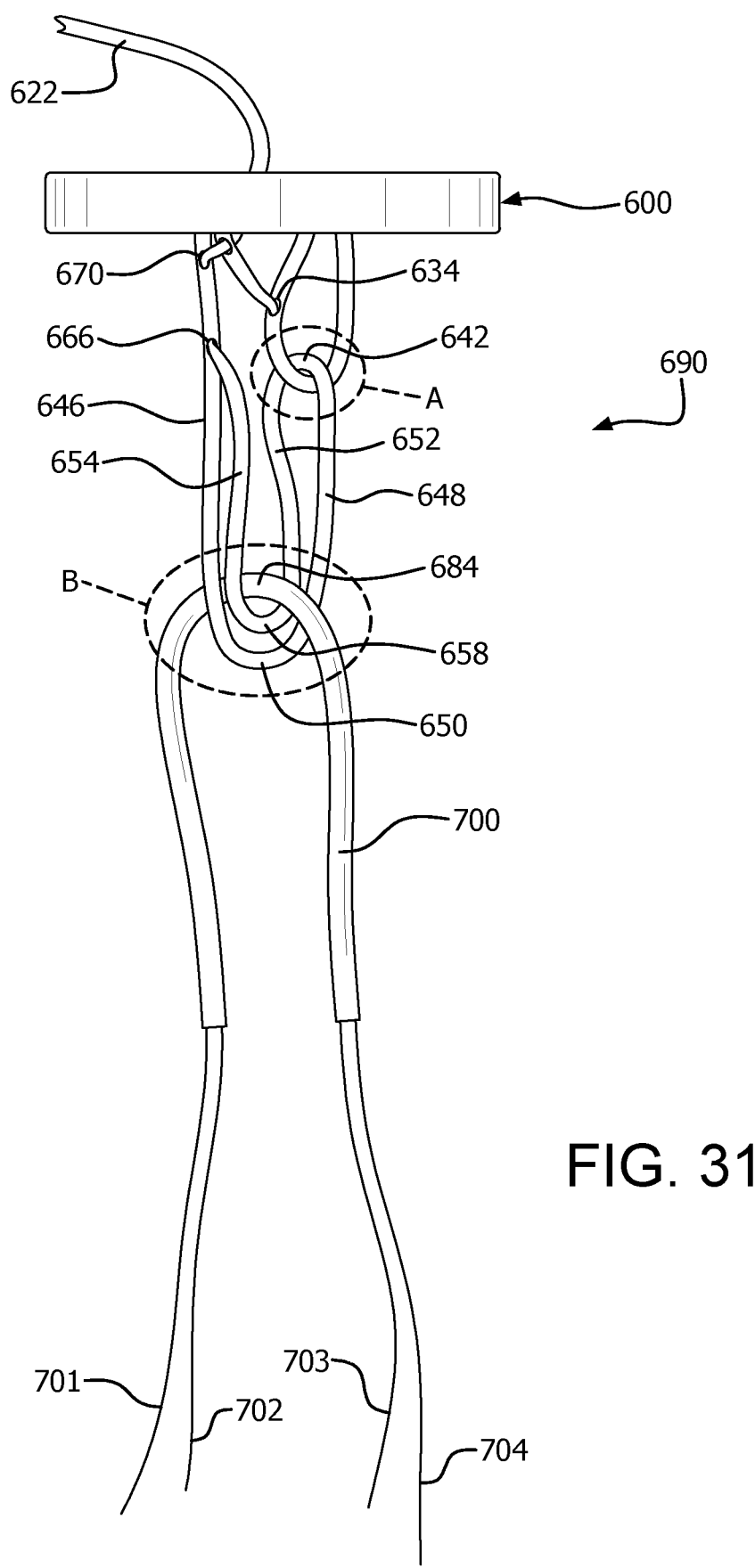
FIG. 31 is a side elevation of an adjustable fixation device and a surgical graft.

There is shown in FIG. 31 a graft 700 in position with the adjustable fixation device 690. The graph 700 can have securing sutures 701-704 at ends thereof. The adjustable fixation device 690 and the graft 700 together form a system similar to pulleys, as indicated by area A and B. In area A, the downward facing bend 642 slidably traverses over the upward facing bend 639 in the manner of a pulley. In area B, portion 684 of graft 700 slidably traverses over the upward facing bend 650 and the upward facing bend 658 in the manner of a pulley. Pulley system A provides a mechanical advantage of 2:1, and pulley system B provides a mechanical advantage of 2:1, so that together pulley system A and pulley system B provide a joint mechanical advantage for the adjustable fixation device 690 of 4:1.

Figure 32:
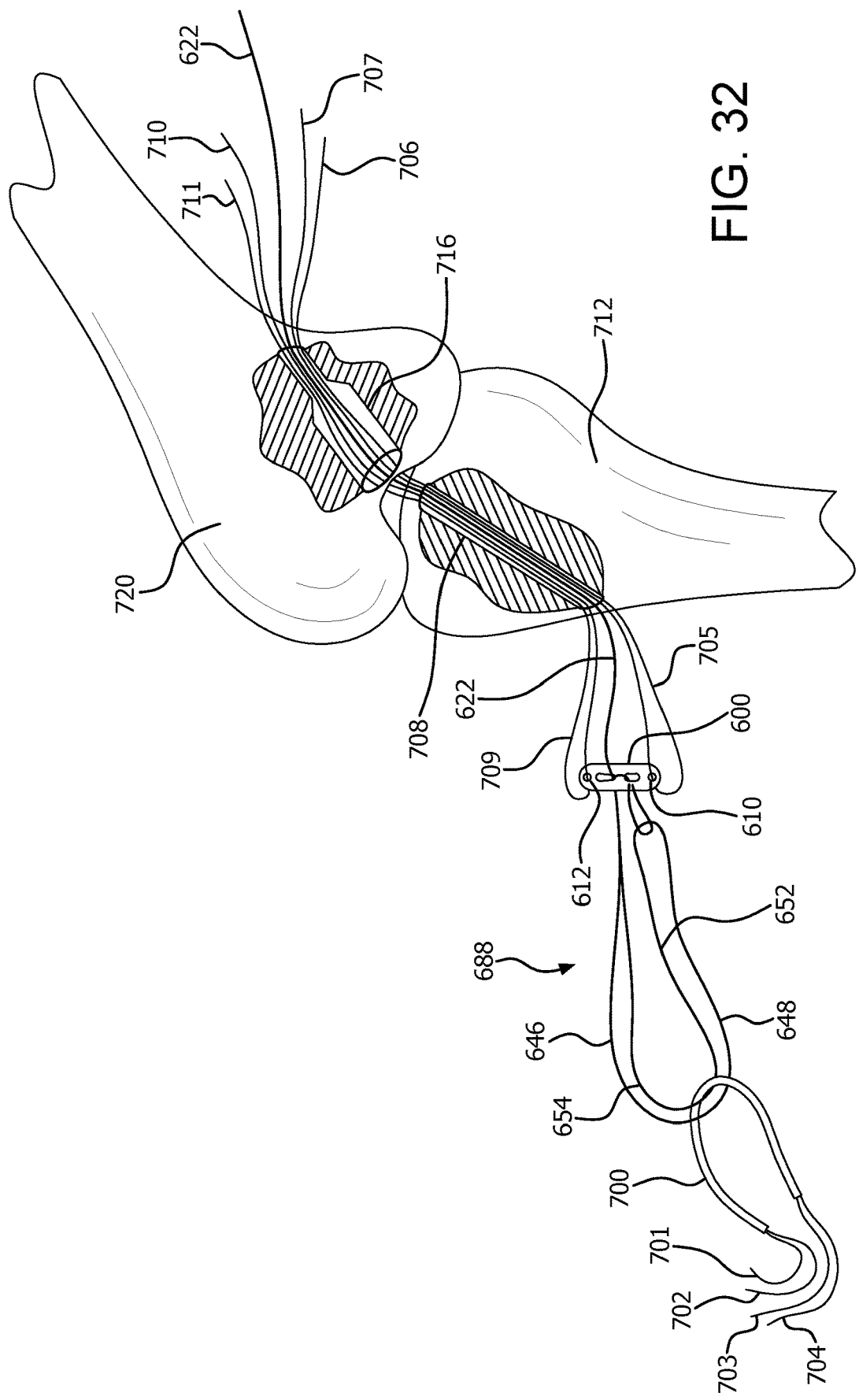
FIG. 32 is a schematic perspective, partially broken away, of an adjustable fixation device according to the invention and a surgical graft being inserted into the femur and tibia in a method according to the invention.

The operation of the adjustable fixation device 690 is shown in FIGS. 32-39. In FIG. 32, a channel 708 is formed in tibia 712. A channel 716 is formed in the femur 720. A guide suture 705 is positioned in aperture 610 of cleat 600 and ends 706 and 707 are threaded through the tibia channel 708 and femur channel 716. A guide suture 709 is positioned in aperture 612 of cleat 600 and ends 710 and 711 are positioned through the tibia channel 708 and femur channel 716. The tensioning tail end 622 of the flexible connector 621 is also positioned through the channel 708 and femur channel 716. The graft 700 is positioned on the adjustable fixation flexible connector portion 688.

Figure 33:
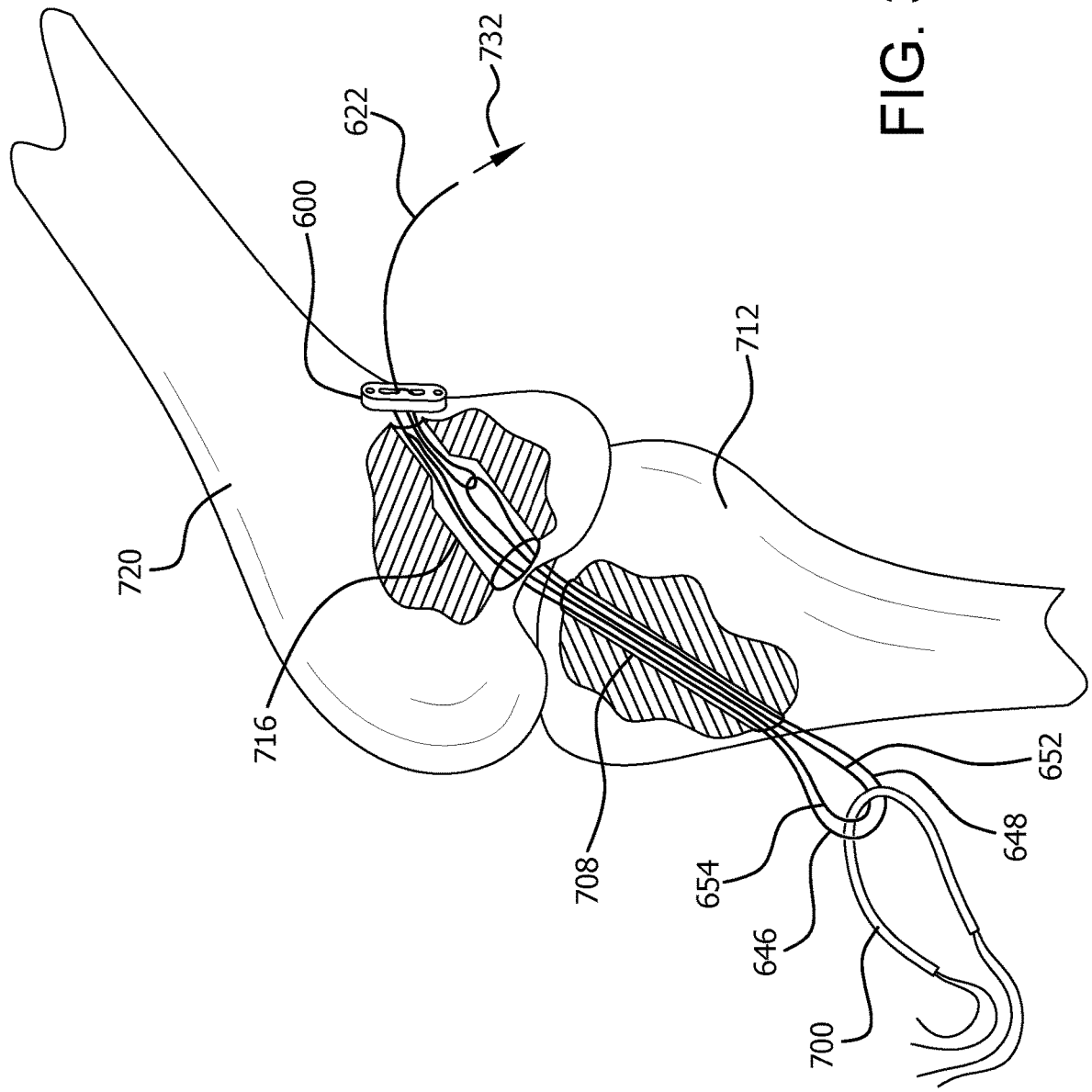
FIG. 33 is a schematic perspective, partially broken away, of an adjustable fixation device and a surgical graft being inserted into the femur and tibia in a subsequent stage of the method.
Figure 34:
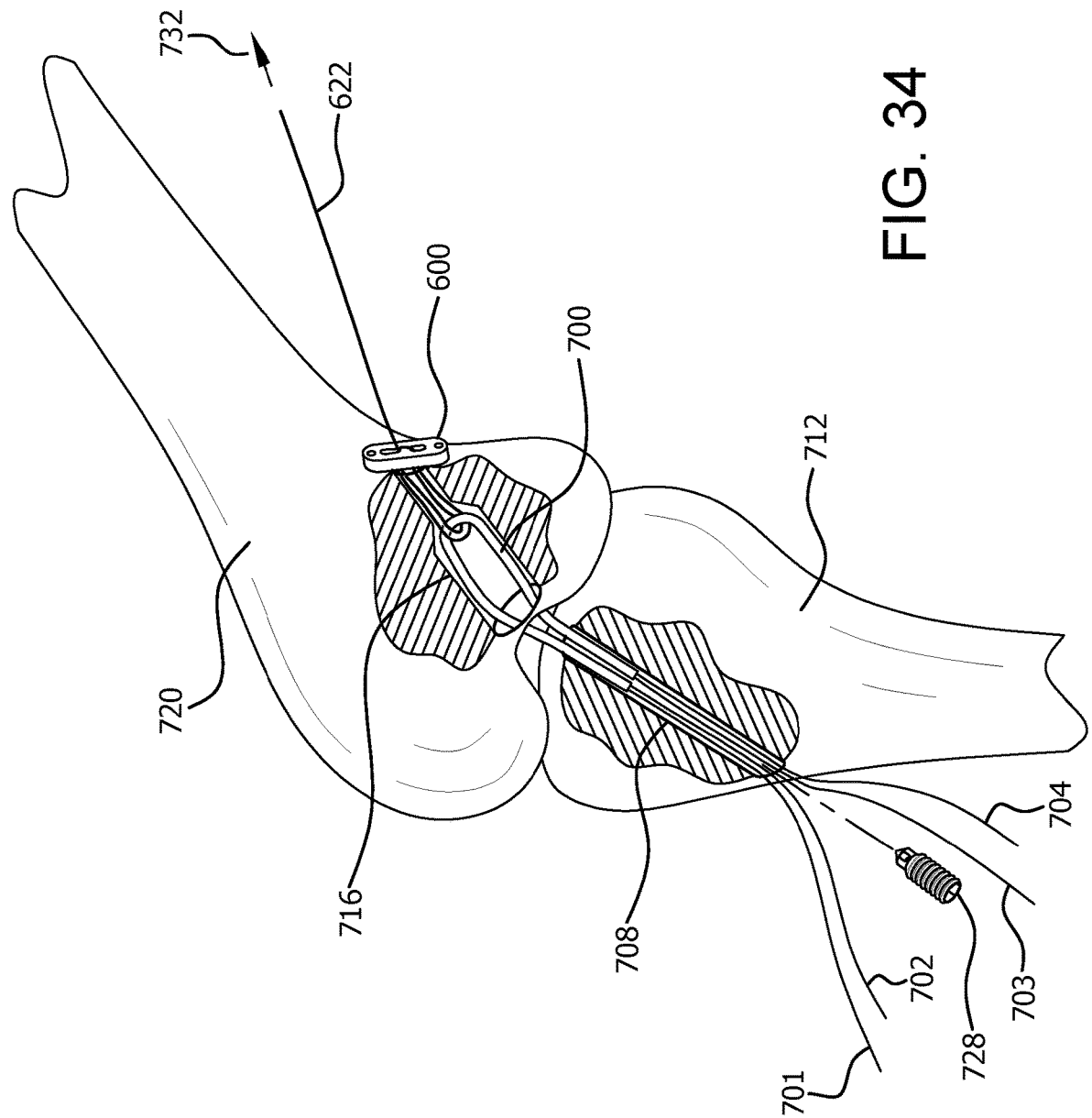
FIG. 34 is a schematic perspective, partially broken away, of an adjustable fixation device in a surgical graft being inserted into the femur and tibia in a stage of the method subsequent to that shown in FIG. 33.
Figure 35:
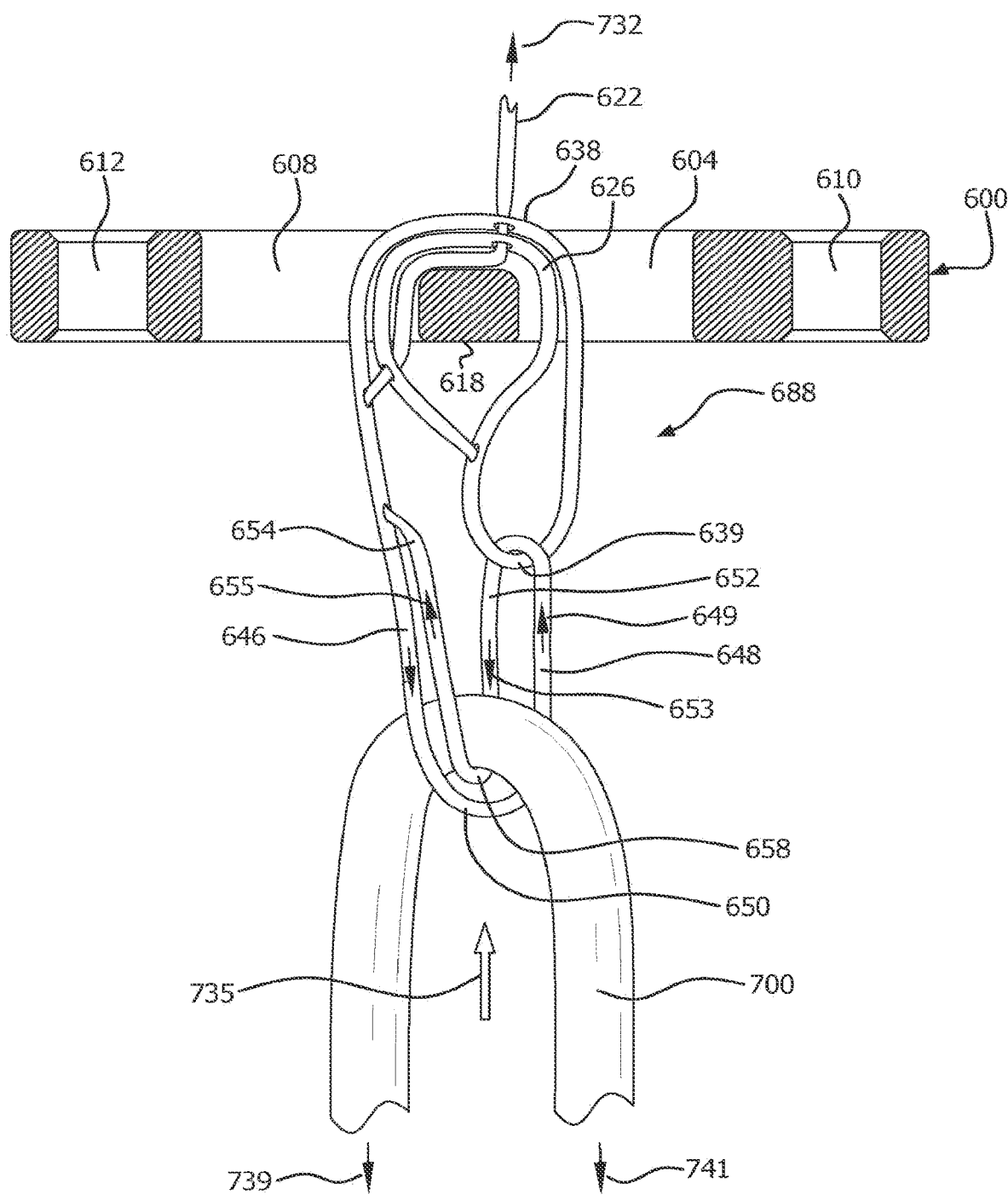
FIG. 35 is a schematic side elevation, partially in cross section, of an adjustable fixation device and a surgical graft in an initial untightened position.

The guide sutures 705 and 709 are then manipulated by the surgeon to draw the cleat 600 through the tibia channel 708 and femur channel 716, as shown in FIG. 33. Tension is placed on tail and 622 as indicated by arrow 732 to draw the adjustable fixation flexible connector portion 688 and the graft 700 toward the cleat 600. The graft 700 will be drawn through the tibia channel 708 and into the femur channel 716 as shown in FIG. 34. The ends of sutures 701-704 will extend from the tibia channel 708 and can be secured by a suture anchor 728 and indicated. Remaining portions of the tail end 622 and the securing sutures 701-704 can be trimmed.

The securing of the cleat 600, adjustable fixation flexible connector portion 688 and grab 700 is shown in FIG. 35-39. Tension is applied to the tail end 622 as indicated by arrow 732. The ascending portion 654 is drawn in the direction indicated by arrow 655 and the descending portion 652 is moved in the direction shown by arrow 653. The ascending portion 648 is moved in the direction indicated by arrow 649, and the upwardly facing bend 650 and upwardly facing bend 658 move upward and engage the graft 700 causing the graft to move upward in the direction indicated by arrow 735. The graft applies a counteracting force against the adjustable fixation flexible connector portion 688 as indicated by arrow 739 and 741.

Figure 36:
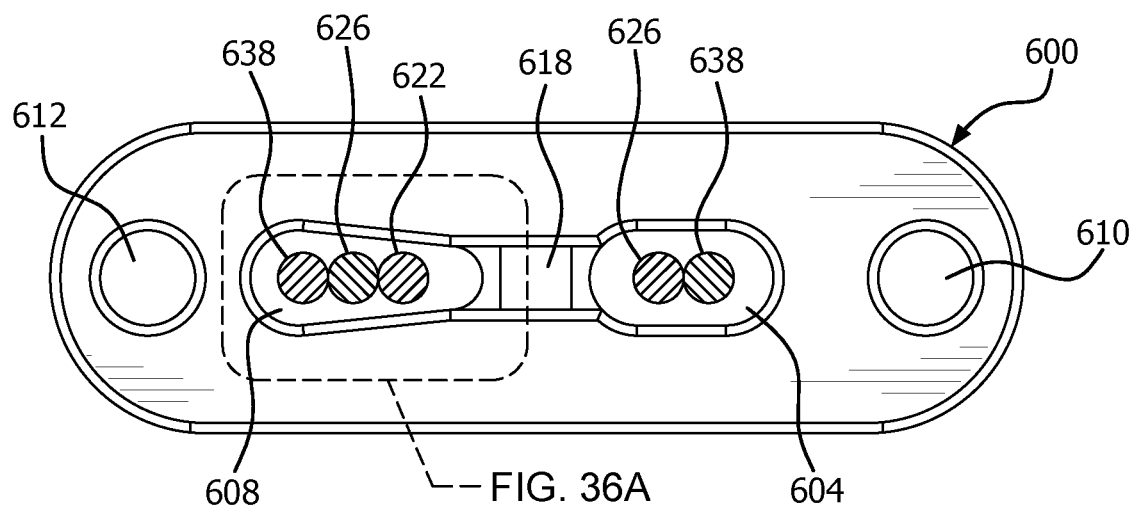
FIG. 36 is a plan view, partially in cross-section, of a cleat and flexible connector of the adjustable fixation device in the initial untightened position.
Figure 36A:
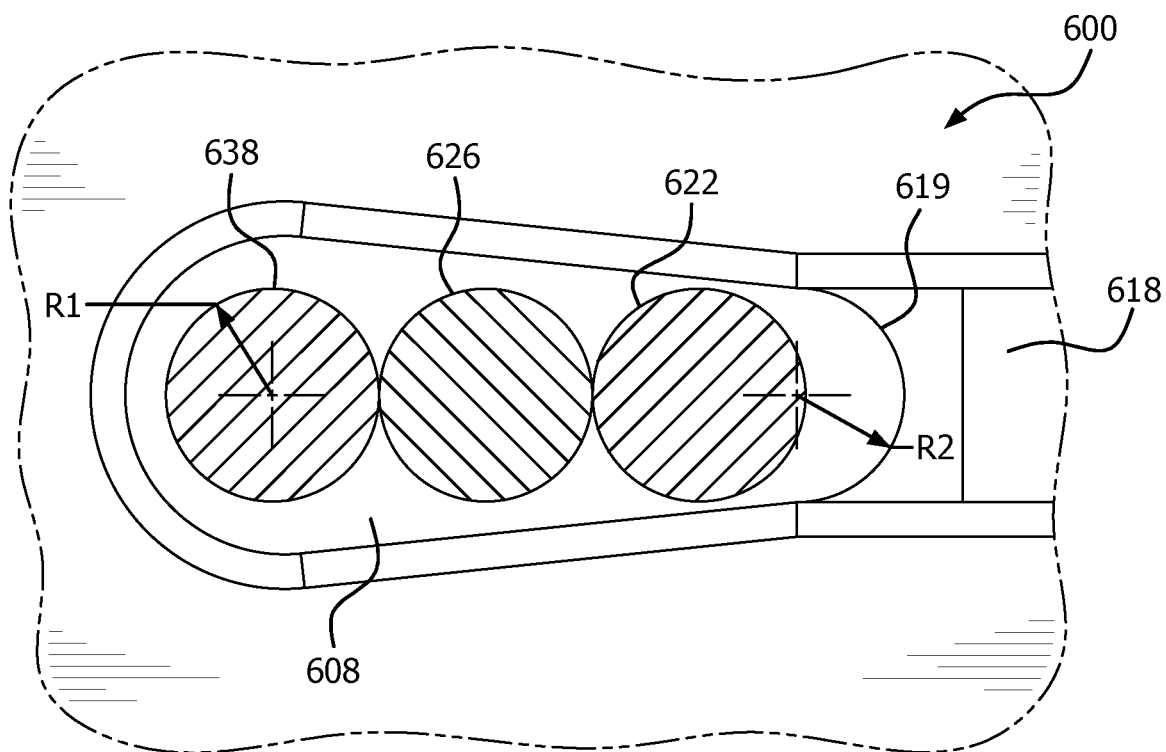
FIG. 36A is an expanded view of area FIG. 36A in FIG. 36.
Figure 37:
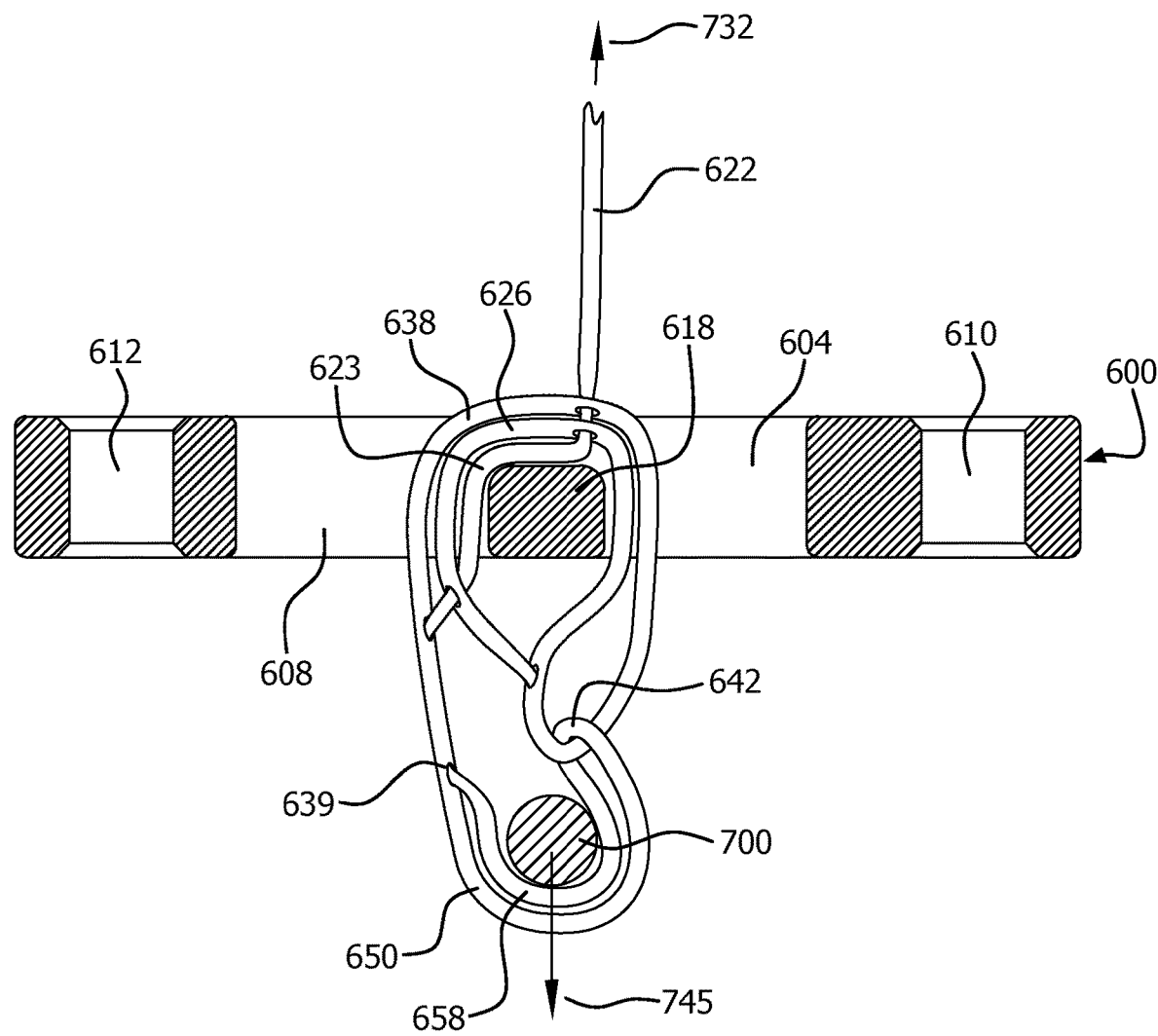
FIG. 37 is a schematic side elevation, partially in cross section, of an adjustable fixation device and a surgical graft in a tightened and secured position.
Figure 38:
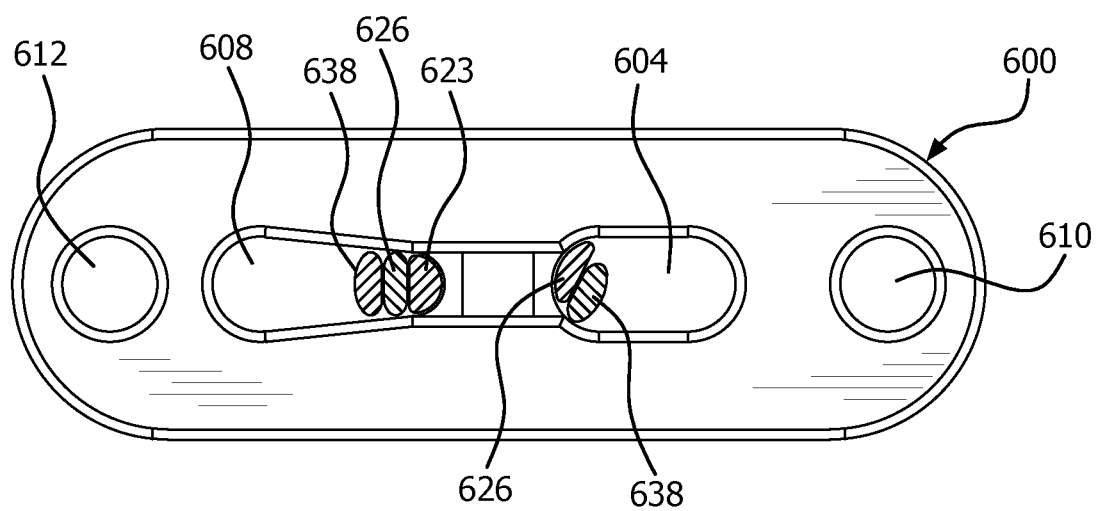
FIG. 38 is a plan view, partially in cross-section, of a cleat and a flexible connector of an adjustable fixation device in a tightened and secured position.
Figure 39:
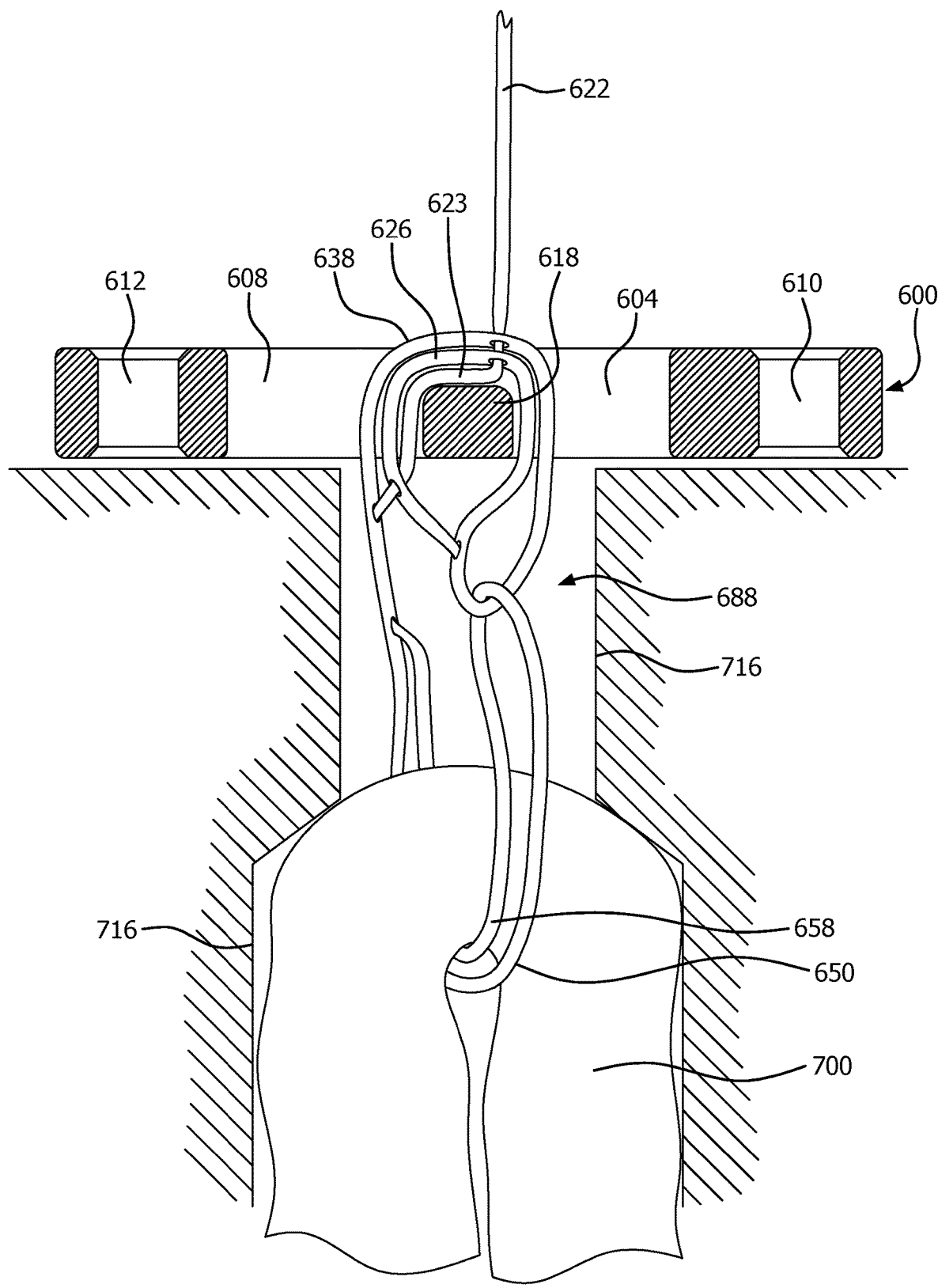
FIG. 39 is a schematic side elevation of an adjustable fixation device and a surgical graft in a tightened and secured position in a femur.

In the initial stages of tensioning, the downwardly facing inner bend 626 and downwardly facing outer 638 are loosely positioned in the oval bore 604 and tapered bore 608, as indicated in FIG. 36. As shown in FIG. 36A, the flexible connector 621 has a radius R1 and the bridge portion 618 has an arcuate surface 619 providing a tapered radius of R2. Increased tension on the tail end 622 is shown in FIG. 37 by arrow 732. The graft 700 continues to apply a downward force as indicated by arrow 745. The portion 623 of the flexible connector 621 is forced against the seat portion 618 of cleat 600 and particularly the arcuate surface 619. The cross-sectional area of the flexible connector 621 is greater than the cross-sectional area defined by the radius R2, and accordingly the portion 623 is wedged into the arc defined by the arcuate surface 619 of the tapered bore 608. This is shown in FIG. 38. The downward facing outer bend 638 is drawn downwards through the tapered bore 608 and toward the seat portion 618, as is the downward facing inner bend portion 626. The portion 623 is thereby firmly locked in position, and will remain locked when the tail end 622 is removed. The graft 700 is thereby securely positioned in the femur channel 716, as shown in FIG. 39.

Figure 40:
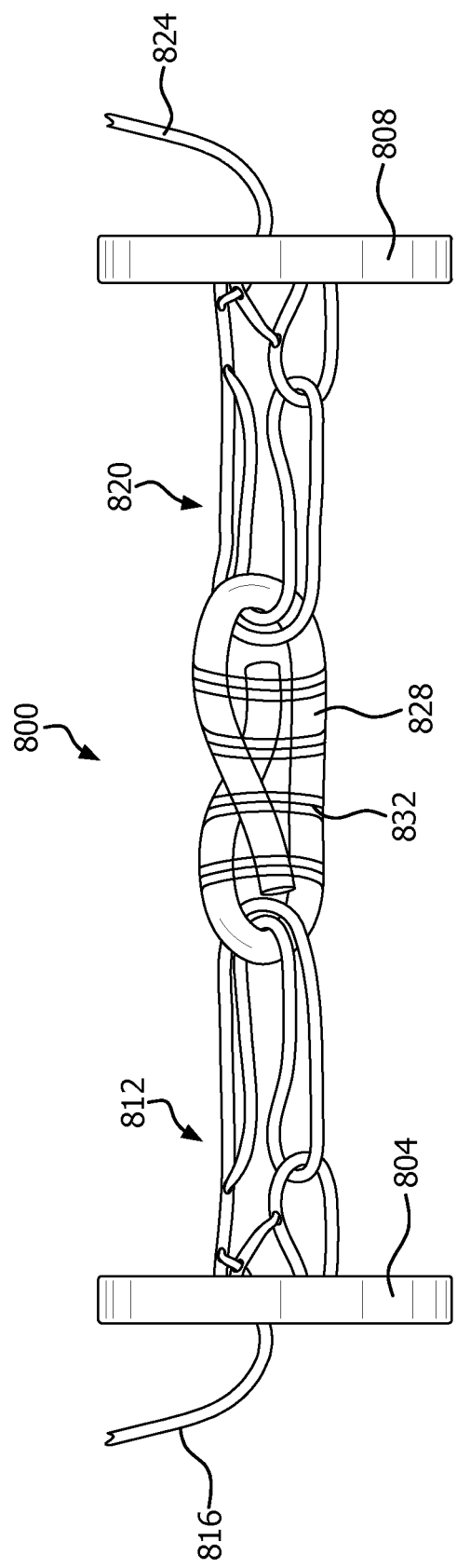
FIG. 40 is a side perspective view of a double-sided embodiment of an adjustable fixation device with a surgical graft.
Figure 41:
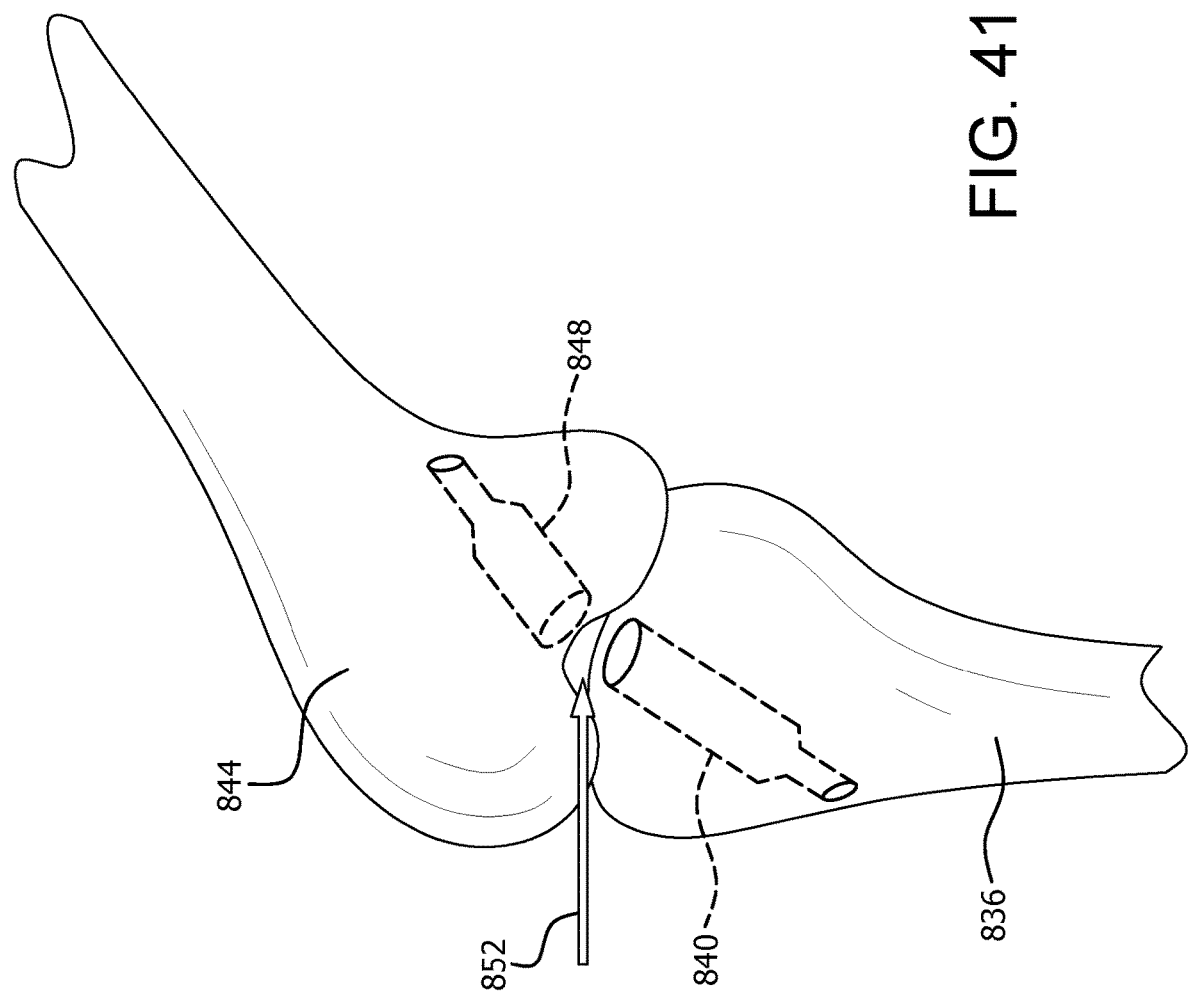
FIG. 41 is a schematic perspective view, partially in phantom, showing an initial step in the insertion of the double-sided embodiment in a tibia and femur.
Figure 42:
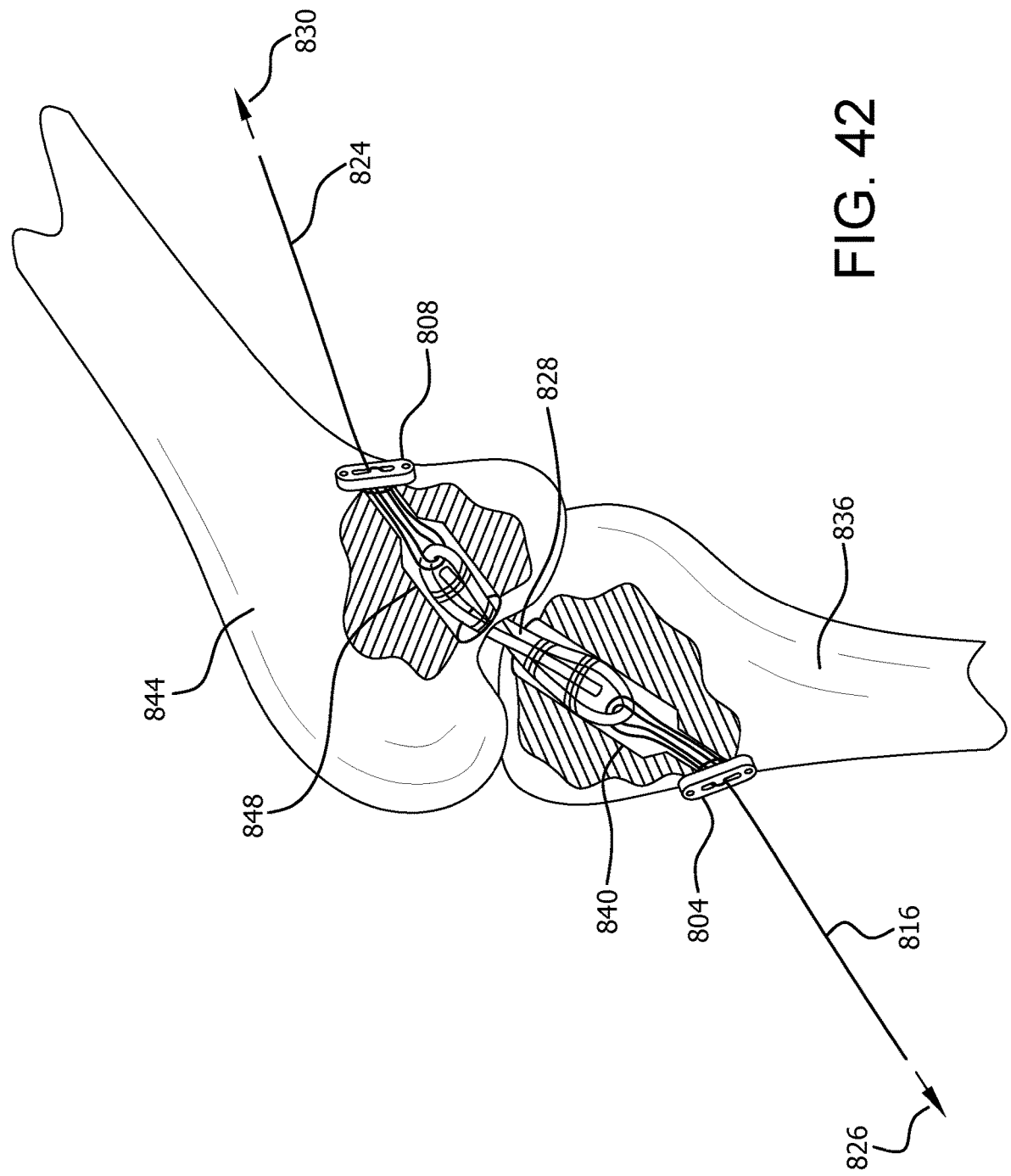
FIG. 42 is a schematic perspective view, partially broken away, showing the completion of the installation of the double-sided embodiment in the tibia and femur.

There is shown in FIGS. 40-42 a double-sided embodiment 800 of the adjustable fixation device. The double-sided embodiment 800 has a first adjustable fixation device 812 and a second adjustable fixation device 820. A graft 828 is disposed between and of the first adjustable fixation device 812 and the second adjustable fixation device 820, and can be secured together by wrapped line or suture 832. The first adjustable fixation device 812 has a cleat 804 and is formed with a flexible connector 816 that includes a tensioning end. The second adjustable fixation device 820 has a cleat 808 and a flexible connector 824 with a tensioning end. The structure and operation of the first adjustable fixation device 812 and the second adjustable fixation device 820 can be similar to that shown in FIGS. 26-39, or in one or more of the other embodiments shown herein.

The installation of the double-sided embodiment 800 is performed between the tibia 836 and femur 844, as indicated by arrow 852 in FIG. 41. A first cavity 840 is formed in the head of the tibia 836. A second cavity 848 is formed in the head of the femur 844. The double-sided embodiment 800 is inserted between the tibia 836 and femur 844 as shown by arrow 852 and FIG. 41. Guide sutures (not shown) are used to guide the first cleat 804 through the first cavity 840, and the second cleat 808 through the second cavity 848, as shown in FIG. 42. The graft 828 is thereby positioned within the first cavity 840 and the second cavity 848. Tension indicated by arrow 826 is applied to the tension end of flexible connector 816, and tension indicated by arrow 830 is applied to the attention end of flexible connector 824. The first adjustable fixation device 812 and second adjustable fixation device 820 can thereby be tightened and secured in place to secure the graft 828 in position.

Figure 43:
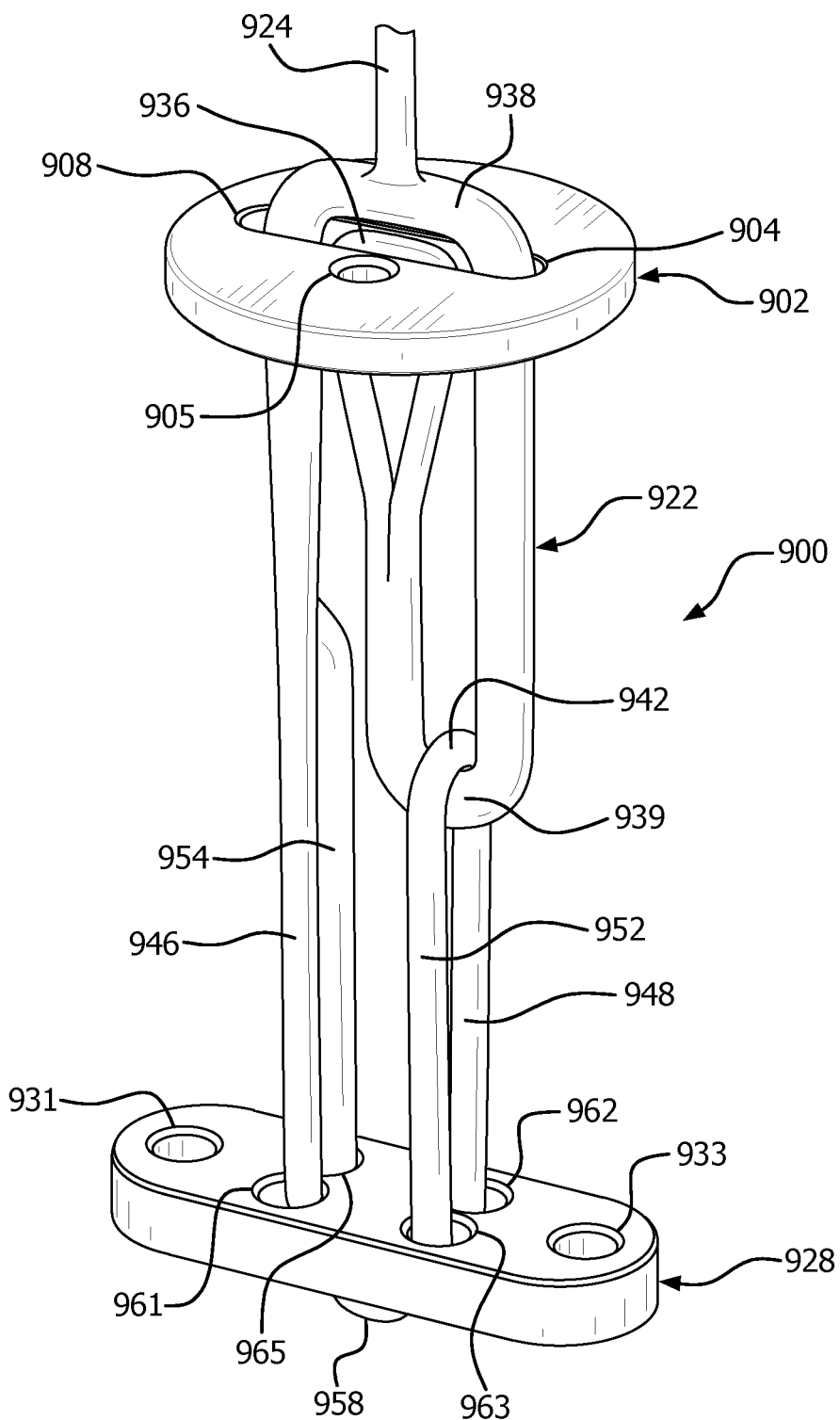
FIG. 43 is a top perspective view of an alternative embodiment of an adjustable fixation device suitable for syndesmosis repair.
Figure 44:
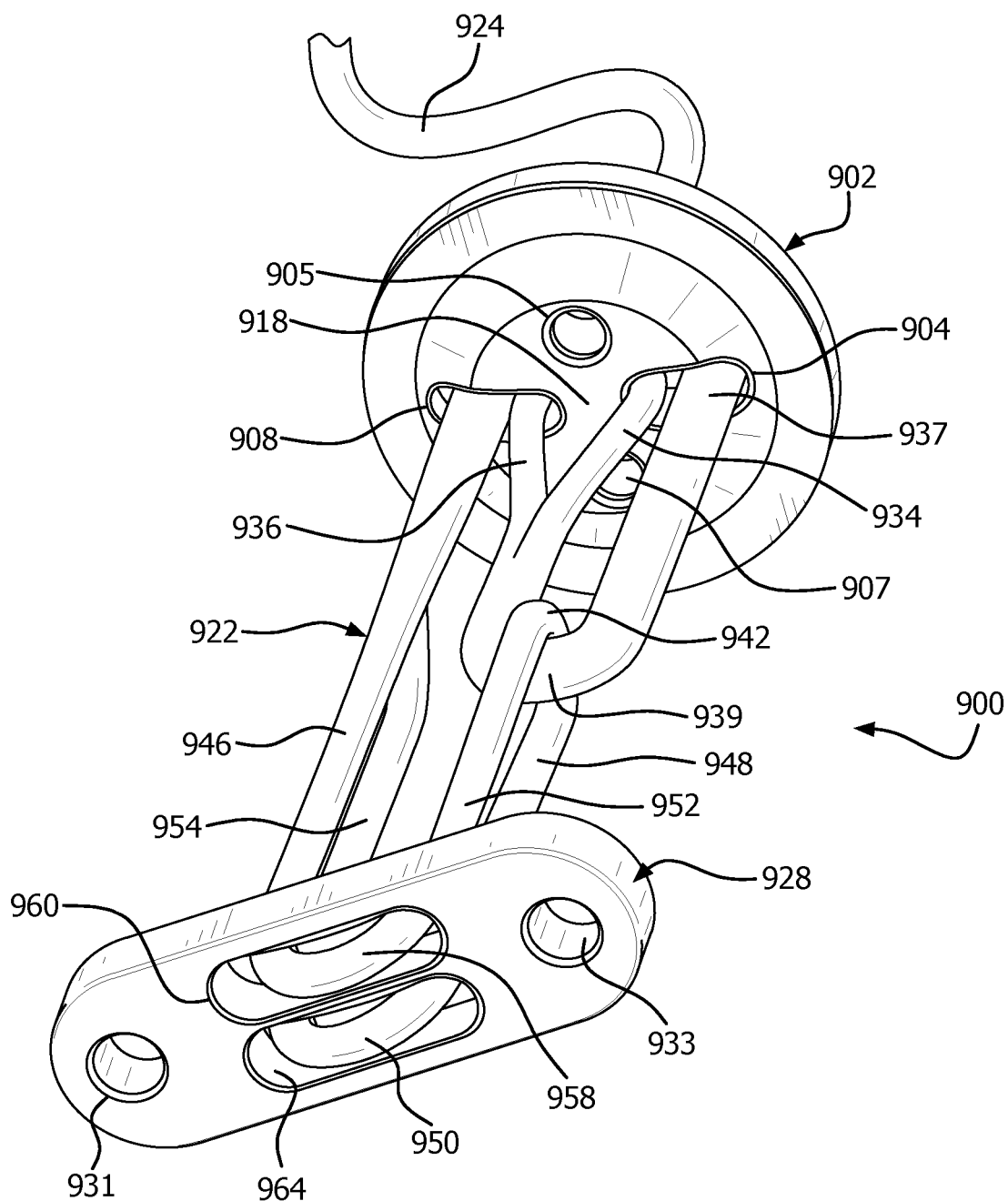
FIG. 44 is a bottom perspective view of the adjustable fixation device of FIG. 43.

There is shown in FIGS. 43-46 an alternative embodiment particularly useful for syndesmosis repair. As shown in FIGS. 43-44, this embodiment 900 of the adjustable fixation device can have a cleat 902 with apertures 904 and 908. A flexible connector portion 922 has a tail 924 and a portion 934 of the flexible connector can pass through the bore 904 and over a seat portion 918 through the bore 908 to form a downward facing inner bend 936. A portion of the flexible connector can be captured longitudinally and secured to itself such that the inner bend 936 forms part of a closed loop. A portion 937 passes through the bore 904 forming an upward facing bend 939. A portion 946 passes through the bore 908 such that a downward facing outer bend portion 938 is over the downward facing inner bend portion 936. The portion 946 can turn upward at an upward facing bend 958 to provide an ascending portion 952.

The ascending portion 952 can pass over the upward facing bend 939 to form a downward facing bend 942 and a descending portion 948. The portion of the flexible connector forming the downward facing bend 942 is slidable relative to the upward facing bend 939, and forms and intra-connector sliding loop engagement portion. The descending portion 948 can turn upward at an upward facing bend 950 and form an ascending portion 954. A portion of the ascending portion 954 is slidably captured longitudinally within the portion 946 and exits as the tail 924.

A second cleat 928 has a groove 960 to receive the upward facing bend 958 and a groove 964 to receive the upward facing bend 950. The groove 960 communicates with apertures 961 and 963. The groove 964 communicates with apertures 962 and 965. The portions of the flexible connector corresponding to the upward facing bend 950 and upward facing bend 958 move within the groove and the apertures to provide a sliding interaction of these portions of the flexible connector with the second cleat 928 and form a connector-device sliding loop engagement portion.

The flexible connector transversely engages the downward facing inner bend 936 and abuts the bridge portion 918 and is positioned between the bridge portion 918 and a corresponding portion of the downward facing bend 936. The flexible connector then transversely passes through the downward facing outer bend 938. The tail 924 will provide tensioning to tension and secure the adjustable fixation device 900 in position.

Figure 45:
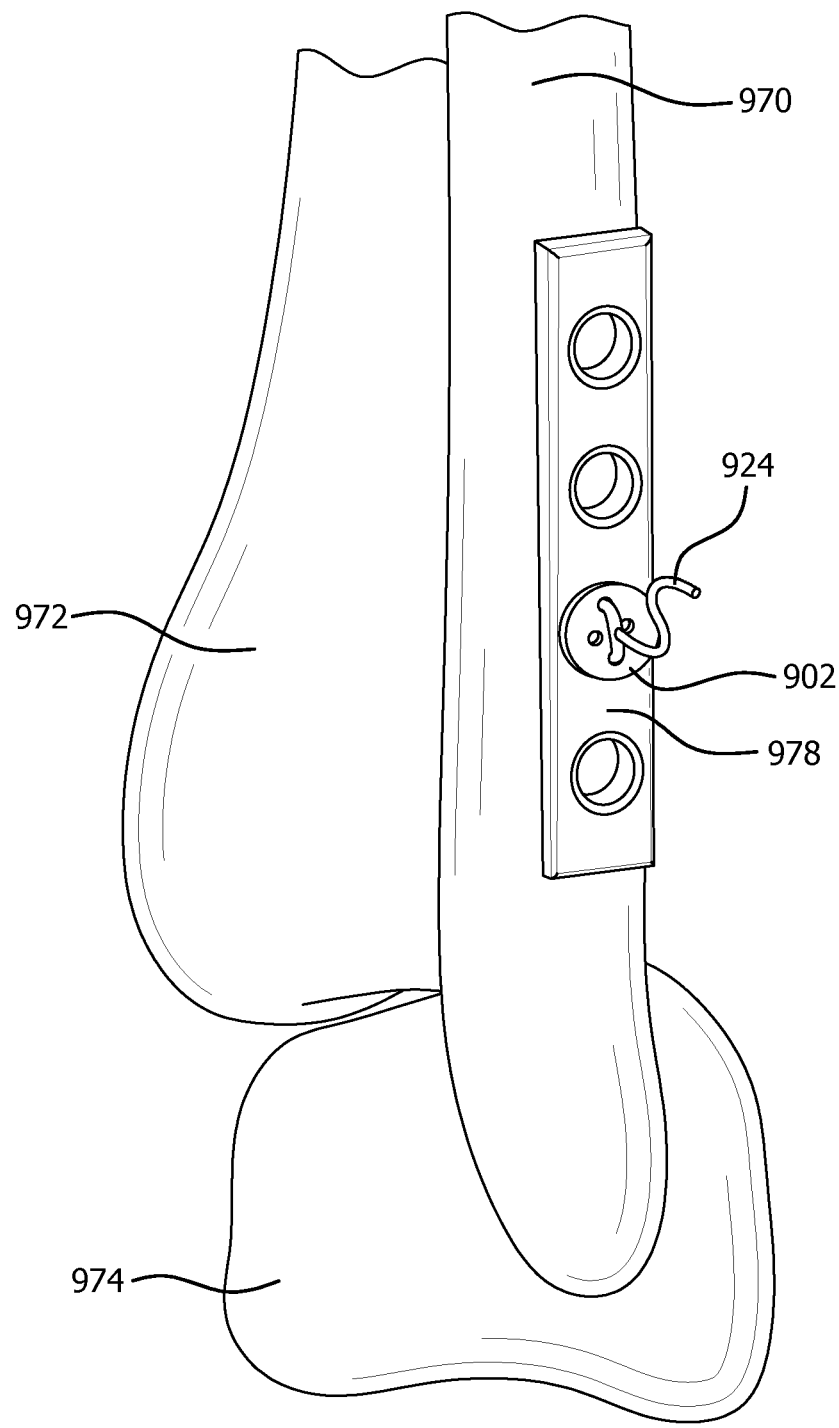
FIG. 45 is a perspective view of the adjustable fixation device for syndesmosis repair of FIG. 43 secured to the tibia and to the fibula.
Figure 46:
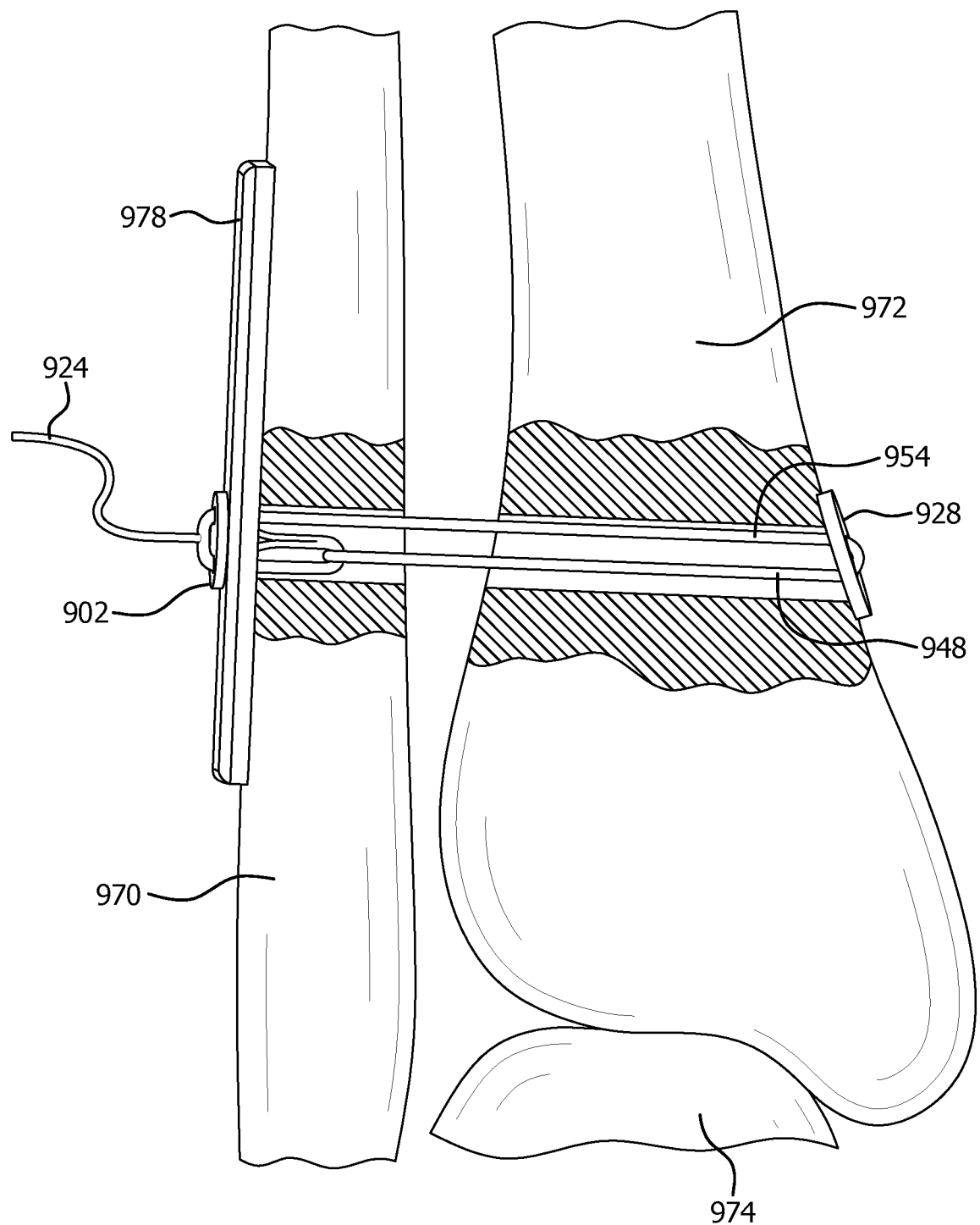
FIG. 46 is a side elevation, partially broken away, of the adjustable fixation device for syndesmosis repair of FIG. 43 secured to the tibia and to the fibula.

A syndesmosis repair is shown in FIGS. 45-46, where the fibula 970 is secured to the tibia 972 over the talus 974. Guide holes 905 and 907 can be provided in the cleat 902 and can be used too position guiding sutures for guiding the cleat 902 into proper position. Guide holes 931 and 933 and can be provided in the cleat 928 to receive guiding sutures for guiding the cleat 928 into proper position. The cleat 902 communicates with a plate 978 to provide support for the fibula 970. A tensioning force is applied to the tensioning end 924 of the flexible connector to draw the second cleat 928 toward the plate 978.

While the exemplary embodiments described above have been chosen primarily from the field of arthroscopic surgery, one of skill in the art will appreciate that the principles of the invention are equally well applied, and that the benefits of the present invention are equally well realized in a wide variety of other surgical and medical systems including, for example, conventional surgery. Further, while the invention has been described in detail in connection with the presently preferred embodiments, it should be readily understood that the invention is not limited to such disclosed embodiments. Rather, the invention can be modified to incorporate any number of variations, alterations, substitutions, or equivalent arrangements not heretofore described, but which are commensurate with the spirit and scope of the invention. Accordingly, the invention is not to be seen as limited by the foregoing description, but is only limited by the scope of the appended claims.

We claim:

1. An adjustable fixation device, comprising:
a first attachment device comprising first and second apertures and lateral and medial sides;
a second attachment device comprising first and second apertures and lateral and medial sides;
said medial sides facing each other;
a flexible connector having first and second ends, the flexible connector connecting the first attachment device and the second attachment device;
the first end of the flexible connector being secured relative to the first attachment device;
the flexible connector forming a first sliding loop bend portion extending medially from the first attachment device and having first and second legs, the first leg extending from the secured first end and the second leg passing through the first and second apertures of the first attachment device to form a sliding elbow connection with the first attachment device;
the flexible connector forming a first connecting arm portion extending from the second aperture of the first attachment device to the first aperture of the second attachment device, the flexible connector continuing from the first aperture of the second attachment device to the second aperture of the second attachment device and extending medially from the second attachment device to form a second sliding loop bend portion having first and second legs;
the first sliding loop bend portion and the second sliding loop bend portion slidably engaging to form an intra-connector sliding loop engagement portion;
the second leg of the second sliding loop bend portion passing through at least one aperture of the second attachment device and forming a second connecting arm extending to the first attachment device and passing through the second aperture of the first attachment device;
the second connecting arm forming a first axial splice by threading the second end of the flexible connector through at least one selected from the group consisting of the first connecting arm and the second leg of the first sliding loop bend portion.

2. The adjustable fixation device of claim 1, wherein the axial splice has an entry location and an exit location on the second leg of the first sliding loop bend portion.

3. The adjustable fixation device of claim 2, wherein the axial splice has an entry location at the sliding elbow portion of the second leg of the first sliding loop bend portion on a lateral side of the first attachment device.

4. The adjustable fixation device of claim 3, wherein the exit location of the axial splice is on a medial side of the first attachment device.

5. The adjustable fixation device of claim 1, wherein the axial splice has an entry location and an exit location on the first connecting arm.

6. The adjustable fixation device of claim 5, wherein the entry location of the axial splice is on a medial side of the first attachment device.

7. The adjustable fixation device of claim 6, wherein the exit location of the axial splice is on a lateral side of the first attachment device.

8. The adjustable fixation device of claim 6, wherein the exit location of the axial splice is on a medial side of the first attachment device.

9. The adjustable fixation device of claim 8, wherein the second end after exiting the exit location of the axial splice is transversely threaded through the sliding elbow connection.

10. The adjustable fixation device of claim 9, wherein the first leg of the first sliding loop bend portion is secured relative to the first attachment device by the first end of the flexible connector passing through the first and second apertures of the first attachment device and being secured to form an eye loop engagement with the first attachment device.

11. The adjustable fixation device of claim 10, wherein the second end after exiting the exit location of the axial splice is transversely threaded through first and second portions of the eye loop.

12. The adjustable fixation device of claim 1, wherein the second leg of the second sliding loop bend portion passes through the second aperture of the second attachment device and forms the second connecting arm.

13. The adjustable fixation device of claim 1, wherein the second attachment device comprises third and fourth apertures, and the flexible connector passes through the third and fourth apertures of the second attachment device.

14. The adjustable fixation device of claim 1, wherein the flexible connector is a suture.

15. The adjustable fixation device of claim 1, wherein at least one selected from the group consisting of the first attachment device and the second attachment device comprises a surgical button.

16. The adjustable fixation device of claim 1, wherein at least one selected from the group consisting of the first attachment device and the second attachment device comprises lateral guide holes for receiving guiding sutures.

17. The adjustable fixation device of claim 1, wherein at least one selected from the group consisting of the first attachment device and the second attachment device comprises structure for engaging a graft.

* * * * *